(12) United States Patent
Gresham et al.

(10) Patent No.: US 8,753,368 B2
(45) Date of Patent: Jun. 17, 2014

(54) SHEATH INTRODUCTION APPARATUS AND METHOD

(75) Inventors: Richard D. Gresham, Guilford, CT (US); Thomas Wenchell, Durham, CT (US); Robert DeSantis, West Redding, CT (US)

(73) Assignee: Covidien LP, Mansfield, MA (US)

( * ) Notice: Subject to any disclaimer, the term of this patent is extended or adjusted under 35 U.S.C. 154(b) by 575 days.

(21) Appl. No.: 13/032,954

(22) Filed: Feb. 23, 2011

(65) Prior Publication Data

US 2011/0144618 A1    Jun. 16, 2011

Related U.S. Application Data

(63) Continuation of application No. 10/720,510, filed on Nov. 24, 2003, now Pat. No. 7,896,897.

(60) Provisional application No. 60/429,049, filed on Nov. 22, 2002.

(51) Int. Cl.
| | |
|---|---|
| A61F 11/00 | (2006.01) |
| A61M 29/00 | (2006.01) |
| A61M 5/178 | (2006.01) |
| A61M 5/00 | (2006.01) |
| A61M 25/00 | (2006.01) |

(52) U.S. Cl.
USPC ...... 606/191; 606/108; 606/198; 604/164.03; 604/171; 604/264

(58) Field of Classification Search
CPC ................ A61B 2017/349; A61B 17/3421; A61B 2017/320044; A61B 18/1487
USPC .............. 606/108, 191; 604/164.03, 264, 171
See application file for complete search history.

(56) References Cited

U.S. PATENT DOCUMENTS

| 668,879 A | 2/1901 | Miller |
|---|---|---|
| 1,213,001 A | 1/1917 | Philips |

(Continued)

FOREIGN PATENT DOCUMENTS

| DE | 198 14 576 A | 10/1999 |
|---|---|---|
| EP | 0 177 177 | 4/1986 |

(Continued)

OTHER PUBLICATIONS

Product Brochure ENDOMED™, Cooper Surgical, Inc. (1992) (2 pages).

(Continued)

*Primary Examiner* — Katherine Dowe
*Assistant Examiner* — Michael Mendoza

(57) ABSTRACT

The present disclosure relates to a sheath system for enabling access through an opening in the body of a patient is provided. The sheath system includes a dilation assembly having a radially expandable tubular sheath defining a lumen having a first cross-sectional area when in a non-expanded condition, and a handle assembly operatively coupled to a proximal end of tubular sheath, the handle assembly defining an aperture formed therein, and a first thread defined on the handle in the aperture thereof. The sheath system further includes an expansion assembly including a tubular member defining a lumen having a second cross-sectional area which is larger than the first cross-sectional area of the tubular sheath of the dilation assembly and having an outer surface defining a second thread, the second thread being arranged for engaging the first thread.

25 Claims, 14 Drawing Sheets

(56) References Cited

U.S. PATENT DOCUMENTS

| | | |
|---|---|---|
| 1,248,492 A | 12/1917 | Hill |
| 2,548,602 A | 4/1951 | Greenburg |
| 3,509,883 A | 5/1970 | Dibelius |
| 3,545,443 A | 12/1970 | Ansari |
| 3,742,958 A | 7/1973 | Rundles |
| 3,788,318 A | 1/1974 | Kim et al. |
| 3,789,852 A | 2/1974 | Kim et al. |
| 3,902,492 A | 9/1975 | Greenhalgh |
| 3,952,748 A | 4/1976 | Kaliher et al. |
| 4,018,230 A | 4/1977 | Ochiai et al. |
| 4,141,364 A | 2/1979 | Schultze |
| 4,411,655 A | 10/1983 | Schreck |
| 4,447,237 A | 5/1984 | Frisch et al. |
| 4,479,497 A | 10/1984 | Fogarty et al. |
| 4,581,025 A | 4/1986 | Timmermans |
| 4,589,868 A | 5/1986 | Dretler |
| 4,601,713 A | 7/1986 | Fuqua |
| 4,610,688 A | 9/1986 | Silvestrini et al. |
| 4,650,466 A | 3/1987 | Luther |
| 4,710,181 A | 12/1987 | Fuqua |
| 4,716,901 A | 1/1988 | Jackson et al. |
| 4,738,666 A | 4/1988 | Fuqua |
| 4,739,762 A | 4/1988 | Palmaz |
| 4,753,636 A | 6/1988 | Free |
| 4,762,128 A | 8/1988 | Rosenbluth |
| 4,772,266 A | 9/1988 | Groshong |
| 4,798,193 A | 1/1989 | Giesy et al. |
| 4,846,791 A | 7/1989 | Hattler et al. |
| 4,865,593 A | 9/1989 | Ogawa et al. |
| 4,869,717 A | 9/1989 | Adair |
| 4,888,000 A | 12/1989 | McQuilkin et al. |
| 4,896,669 A | 1/1990 | Bhate et al. |
| 4,899,729 A | 2/1990 | Gill et al. |
| 4,921,479 A | 5/1990 | Grayzel |
| 4,941,874 A | 7/1990 | Sandow et al. |
| 4,954,126 A | 9/1990 | Wallsten |
| 4,955,895 A | 9/1990 | Sugiyama et al. |
| 4,972,827 A | 11/1990 | Kishi et al. |
| 4,986,830 A | 1/1991 | Owens et al. |
| 5,021,241 A | 6/1991 | Yamahira et al. |
| 5,045,056 A | 9/1991 | Bwhl |
| 5,078,736 A | 1/1992 | Behl |
| 5,084,057 A | 1/1992 | Green et al. |
| 5,100,388 A | 3/1992 | Behl et al. |
| 5,100,420 A | 3/1992 | Green et al. |
| 5,104,382 A | 4/1992 | Brinkerhoff et al. |
| 5,112,304 A | 5/1992 | Barlow et al. |
| 5,116,318 A | 5/1992 | Hillstead |
| 5,122,122 A | 6/1992 | Allgood |
| 5,139,511 A | 8/1992 | Gill et al. |
| 5,158,545 A | 10/1992 | Trudell et al. |
| 5,183,464 A | 2/1993 | Dubrul et al. |
| 5,188,602 A | 2/1993 | Nichols |
| 5,201,756 A | 4/1993 | Horzewski et al. |
| 5,222,938 A | 6/1993 | Behl |
| 5,222,971 A | 6/1993 | Willard et al. |
| 5,234,425 A | 8/1993 | Fogarty et al. |
| 5,246,424 A | 9/1993 | Wilk |
| 5,250,025 A | 10/1993 | Sosnowski et al. |
| 5,250,033 A | 10/1993 | Evans et al. |
| 5,275,611 A | 1/1994 | Behl |
| 5,279,554 A | 1/1994 | Turley |
| 5,290,276 A | 3/1994 | Sewell, Jr. |
| 5,304,119 A | 4/1994 | Balaban et al. |
| 5,312,360 A | 5/1994 | Behl |
| 5,316,360 A | 5/1994 | Feikema |
| 5,320,611 A | 6/1994 | Bonutti et al. |
| 5,364,372 A | 11/1994 | Danks et al. |
| 5,383,859 A | 1/1995 | Sewell, Jr. |
| 5,392,766 A | 2/1995 | Masterson et al. |
| 5,403,278 A | 4/1995 | Ernst et al. |
| 5,407,430 A | 4/1995 | Peters |
| 5,431,655 A | 7/1995 | Melker et al. |
| 5,431,676 A | 7/1995 | Dubrul et al. |
| 5,433,708 A | 7/1995 | Nichols et al. |
| 5,437,631 A | 8/1995 | Janzen |
| 5,437,644 A | 8/1995 | Nobles |
| 5,453,094 A | 9/1995 | Metcalf et al. |
| 5,454,790 A | 10/1995 | Dubrul |
| 5,454,825 A | 10/1995 | Van Leeuwen et al. |
| 5,460,170 A | 10/1995 | Hammerslag |
| 5,484,403 A | 1/1996 | Yoakum et al. |
| 5,487,739 A | 1/1996 | Aebischer et al. |
| 5,540,658 A | 7/1996 | Evans et al. |
| 5,542,928 A | 8/1996 | Evans et al. |
| 5,573,517 A | 11/1996 | Bonutti et al. |
| 5,601,559 A | 2/1997 | Melker et al. |
| 5,662,614 A | 9/1997 | Edoga |
| 5,674,240 A | 10/1997 | Bonuutti et al. |
| 5,713,867 A | 2/1998 | Morris |
| 5,735,867 A | 4/1998 | Golser et al. |
| 5,746,720 A | 5/1998 | Stouder, Jr. |
| 5,800,390 A | 9/1998 | Hayakawa et al. |
| 5,800,409 A | 9/1998 | Bruce |
| 5,814,058 A | 9/1998 | Carlson et al. |
| 5,824,002 A | 10/1998 | Gentelia et al. |
| 5,827,227 A | 10/1998 | DeLago |
| 5,827,319 A | 10/1998 | Carlson et al. |
| 5,836,913 A | 11/1998 | Orth et al. |
| 5,873,854 A | 2/1999 | Wolvek |
| 5,882,345 A | 3/1999 | Yoon |
| 5,902,282 A | 5/1999 | Balbierz |
| 5,911,714 A | 6/1999 | Wenstrom, Jr. |
| 5,944,691 A | 8/1999 | Querns et al. |
| 5,957,902 A | 9/1999 | Teves |
| 5,961,499 A | 10/1999 | Bonutti et al. |
| 5,971,958 A | 10/1999 | Zhang |
| 5,971,960 A | 10/1999 | Flom et al. |
| 6,030,364 A | 2/2000 | Durgin et al. |
| 6,063,060 A | 5/2000 | Moenning |
| 6,077,248 A | 6/2000 | Zumschlinge |
| 6,080,174 A | 6/2000 | Dubrul et al. |
| 6,083,241 A | 7/2000 | Longo et al. |
| 6,095,967 A | 8/2000 | Black et al. |
| 6,146,400 A | 11/2000 | Hahnen |
| 6,162,236 A | 12/2000 | Osada |
| 6,210,376 B1 | 4/2001 | Grayson |
| 6,235,020 B1 | 5/2001 | Cheng et al. |
| 6,245,052 B1 | 6/2001 | Orth et al. |
| 6,283,950 B1 | 9/2001 | Appling |
| 6,293,909 B1 | 9/2001 | Chu et al. |
| 6,306,124 B1 | 10/2001 | Jones et al. |
| 6,325,789 B1 | 12/2001 | Janzen et al. |
| 6,325,812 B1 | 12/2001 | Dubrul et al. |
| 6,767,355 B2 | 7/2004 | Frova et al. |
| 7,449,011 B2 | 11/2008 | Wenchell et al. |

FOREIGN PATENT DOCUMENTS

| | | |
|---|---|---|
| EP | 0 385 920 | 9/1990 |
| GB | 2199247 | 7/1988 |
| WO | WO 92/19312 | 11/1992 |
| WO | WO 94/20026 | 9/1994 |
| WO | WO 95/30374 | 11/1995 |
| WO | WO 96/02180 | 2/1996 |
| WO | WO 98 19730 A | 5/1998 |

OTHER PUBLICATIONS

Product Brochure BLUNTPORT, Auto Suture Company, a division of United States. Surgical Corporation (1992) (1 pgae).
Product Brochure DEXIDE® Inc., Dexide, Inc. (1992) (1 page).
Product Brochure EXPANDO®, Bentley Harris (1988, 1990, 1991) (12 pages).

SHEATH INTRODUCTION APPARATUS AND METHOD

CROSS-REFERENCE TO RELATED APPLICATION

The present application is a Continuation Application that claims the benefit of and priority to U.S. patent application Ser. No. 10/720,510, filed on Nov. 24, 2003 (now U.S. Pat. No. 7,896,897), which claims the benefit of and priority to U.S. Provisional Application Ser. No. 60/429,049 filed on Nov. 22, 2002, the entire contents of each of which being incorporated herein by reference.

BACKGROUND

1. Technical Field

The present disclosure relates to surgical instrument introduction systems and methods of use and, more particularly, to introduction systems utilizing radially expandable sheaths and which enable a relatively large access area through a relatively small incision and methods of using the same.

2. Background of Related Art

Surgical staplers for applying an annular array of staples to tissue are well known in the art. These staplers typically include a stapling assembly provided at a distal end. The stapling assembly generally includes an array of staples, an anvil and structure for expelling the staples against the anvil. The anvil includes a corresponding array of bucket-shaped members against which the staples are formed.

Surgical staplers for applying an annular array of staples are well known in gastric and esophageal surgery. These staplers are used to form anastomosis in an end-to-end, end-to-side or side-to-side manner. One such instrument is the Premium Plus CEEA™ surgical stapler, manufactured and sold by Autosuture, a division of United States Surgical Corporation, Norwalk, Conn. In use, the instrument is positioned within the lumen of an organ such as the stomach, esophagus or intestine in order to perform an anastomosis. The tissue is positioned between the anvil and the cartridge having the staples. The tissue is then tied off, for example, by a purse string suture. Thereafter, the anvil member is advanced toward the cartridge by rotation of a rotatable knob or wing nut assembly at the proximal end of the instrument. When proper approximation is achieved, the staples are expelled from the cartridge. A circular knife typically follows the formation of the staples to excise unwanted tissue at the anastomosis site. The instrument is then removed from the lumen of the organ.

The recent interest in laparoscopic surgical procedures is attributed to the reduced recovery time and pain associated with utilizing a smaller incision to gain entry into the body. Mechanical devices particularly adapted for use in a laparoscopic environment, in which the abdomen is inflated with insufflation gas to provide working space for the surgeon, have been developed. For example, U.S. Pat. Nos. 5,084,057 and 5,100,420 to Green, et al., the entire contents of which are incorporated herein by reference, describe an endoscopic multiple clip applier which enabled the surgical community to fully realize the potential of endoscopic cholycystectomy. The Green '057 and '420 patents describe, inter alia, gaseous seal means for obstructing and/or restricting the passage of gas from the insufflated body cavity out through the surgical instrument itself.

In commonly assigned U.S. Pat. No. 5,454,825 to Van Leeuwen et al., the entire contents of which is herein incorporated by reference, there is disclosed a circular anastomosis device having at least one seal for preventing the flow of gas through the instrument during surgical procedures.

While providing a sealing system within a circular anastomosis instrument is recognized in the art, the need exists for a sealing system which effectively provides a seal around the exterior of the instrument (i.e., between the instrument and the patient's body) in order to maintain the atmospheric integrity within the body cavity and which enables a relatively large access into a patient through a relatively small opening.

One known system provides a seal between laparoscopic instruments and the incision, and also minimizes the incision size while providing access by radially expanding the incision. For example, U.S. Pat. No. 5,431,676 discloses in certain embodiments a radially expandable dilation member that is introduced through a relatively small incision. The entire disclosure of U.S. Pat. No. 5,431,676 is hereby incorporated by reference herein. An expansion member is used to radially expand the dilation member, and provide access for instruments. In expanding the dilation member, a force must be applied to introduce the expansion member into the dilation member. It is desirable to provide a means for reducing the force required to introduce the expansion member and expand the dilation member.

SUMMARY

The present disclosure relates to introduction systems utilizing radially expandable sheaths and which enable a relatively large access area through a relatively small incision and methods of using the same.

According to one aspect of the present disclosure a sheath system for enabling access through an opening in the body of a patient is provided. The sheath system includes a dilation assembly having a radially expandable tubular sheath defining a lumen having a first cross-sectional area when in a non-expanded condition, and a handle assembly operatively coupled to a proximal end of the tubular sheath, the handle assembly defining an aperture formed therein, and a first thread defined on the handle in the aperture thereof. The sheath system further includes an expansion assembly including a tubular member defining a lumen having a second cross-sectional area which is larger than the first cross-sectional area of the tubular sheath of the dilation assembly and having an outer surface defining a second thread, the second thread being arranged for engaging the first thread.

The sheath system can further include an introducer sized for receipt in the lumen of the radially expandable sheath, when the radially expandable sheath is in the non-expanded condition.

It is envisioned that the tubular member of the expansion assembly is configured and dimensioned to be removably received within the aperture formed in the handle assembly of the dilation assembly.

The tubular sheath of the dilation assembly includes a mesh of individual filaments. Preferably, the filaments are inelastic so that radial expansion of the tubular sheath causes axial shortening of the tubular sheath. Alternatively, the tubular sheath can include a tubular braid of individual filaments.

Desirably, the shaft of the introducer is removably receivable within the lumen of the tubular sheath.

Distal advancement of the tubular member of the expansion assembly desirably results in radial expansion of the tubular sheath from the first cross-sectional area to the second cross-sectional area.

It is envisioned that the sheath system further includes a seal at the proximal end of the expansion assembly. Preferably, the seal is made from at least one of an elastomeric polymeric material and polyisoprene.

It is further envisioned that the sheath system further includes a dilator configured and dimensioned to be removably received within the lumen of the tubular member of the expansion assembly. Preferably, a distal end of the dilator is tapered. More preferably, the distal end of the dilator defines threads. The dilator has a length such that when the dilator is received within the lumen of the tubular member, the tapered distal end thereof extends beyond a distal end of the tubular member. The shaft of the introducer has a length such that when the introducer is received within the lumen of the tubular sheath, a distal end thereof extends beyond a distal end of the tubular sheath.

It is further envisioned that the sheath system can include a converter configured and dimensioned to be removably attached to a proximal end of the expansion assembly. The converter includes an aperture formed therein, wherein the aperture of the converter has a cross-sectional area less than a cross-sectional area of the opening formed in the seal of the expansion assembly.

According to another aspect of the present disclosure, a method of using a sheath system to enable access through an opening in the body of a patient is provided. The method includes the step of inserting a dilation assembly, having a radially expandable sheath defining a lumen and a proximal housing defining an aperture and a first thread in the aperture, into the opening in the body of the patient. The method further includes the step of introducing an expansion assembly, having a tubular member with an outer surface defining a second thread, into the lumen of the dilation assembly to radially expand the lumen of dilation assembly and the opening in the body of the patient, the introduction including engaging the first thread with the second thread.

The method can further include the step of inserting an introducer into the dilation assembly prior to the step of inserting the dilation assembly. The method can still further include the step of inserting a dilator into the expansion assembly prior to the step of introducing the expansion assembly.

It is envisioned that the lumen of the dilation assembly has a first cross-sectional area and the lumen of the expansion assembly has a cross-sectional area which is larger that the first cross-sectional area of the lumen of the dilation assembly.

The sheath can be made from a mesh of individual filaments. Accordingly, upon radial expansion of the tubular sheath causes axial shortening of the sheath.

It is envisioned that introduction of the expansion assembly includes distal advancement of the tubular member of the expansion assembly through the sheath of the dilation assembly, resulting in radial expansion of the sheath.

It is further envisioned that engagement of the first thread with the second thread includes rotation of the tubular member with respect to the dilation assembly.

The expansion assembly can include a seal disposed across the lumen of the tubular member, the seal including an opening formed therein. Accordingly, the method can include the step of introducing an instrument into the tubular member through the opening of the seal.

It is further envisioned that the method can include removably attaching a converter to a proximal end of the tubular member, wherein an opening formed in the converter has a cross-sectional area which is less than the cross-sectional area of the opening formed within the seal.

According to another aspect of the present disclosure, a further method of providing access through an opening in the body of a patient is provided. The method can include the steps of making a skin incision; inserting into the skin incision a dilation assembly, having a radially expandable sheath defining a lumen and a blunt introducer disposed in the lumen; removing the blunt introducer from the lumen; and introducing an expansion assembly, having a tubular member into the lumen of the dilation assembly to radially expand the lumen of the dilation assembly and the incision in the body of the patient.

It is envisioned that a dilator can be disposed in the tubular member when the expansion assembly is introduced into the lumen of the dilation assembly.

These and other features of the sheath system and method disclosed herein will become apparent through reference to the following description of embodiments, the accompanying drawings and the claims.

BRIEF DESCRIPTION OF THE DRAWINGS

The accompanying drawings, which are incorporated in and constitute a part of this specification, illustrate embodiments of the disclosure and, together with the general description given above, and the detailed description of the embodiments given below, serve to explain the principles of the present disclosure.

DETAILED DESCRIPTION OF PREFERRED EMBODIMENTS

Figure 1:
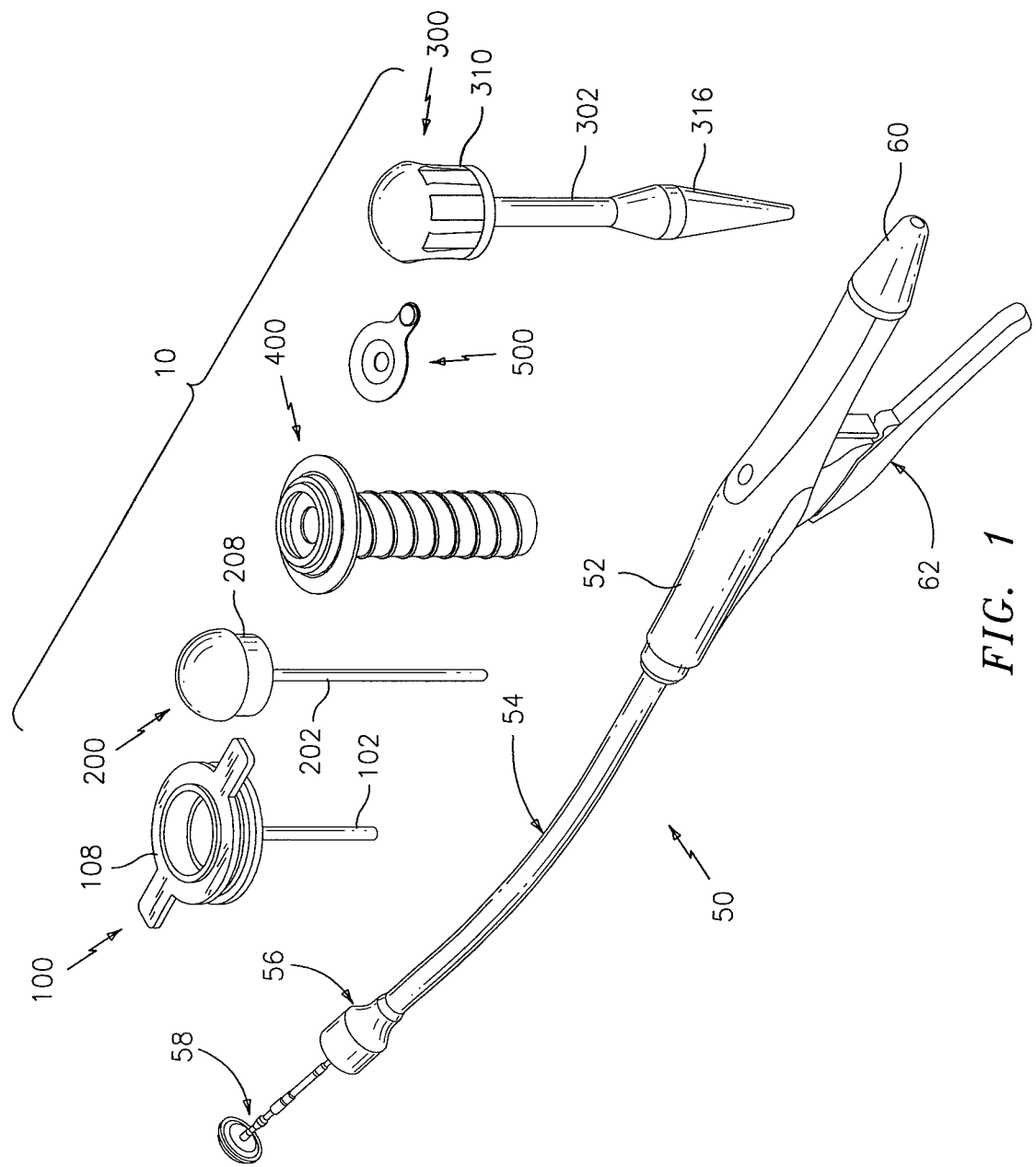
FIG. 1 is a perspective view illustrating the components of a sheath system, in accordance with an embodiment of the present disclosure, for use with a surgical stapling apparatus.

Preferred embodiments of the presently disclosed sheath system will now be described in detail with reference to the drawing figures wherein like reference numerals identify similar or identical elements. In the drawings and in the description which follows, the term "proximal", as is traditional, will refer to the end of the sheath system of the present disclosure which is closest to the operator, while the term "distal" will refer to the end of the sheath system which is furthest from the operator.

A sheath system in accordance with an embodiment of the present disclosure is shown in FIGS. 1 and 3-11 and is generally designated 10. In accordance with the present disclosure, sheath system 10 is configured and adapted to cooperate with an end-to-end, end-to-side or side-to-side surgical anastomosis apparatus. In accordance with the present disclosure, and as will be described individually in greater detail below, sheath system 10 includes: a radially expandable dilation assembly 100; and an expansion assembly 400. Sheath system 10 desirably includes an introducer 200, a dilator 300, and a converter 500.

Figure 2:
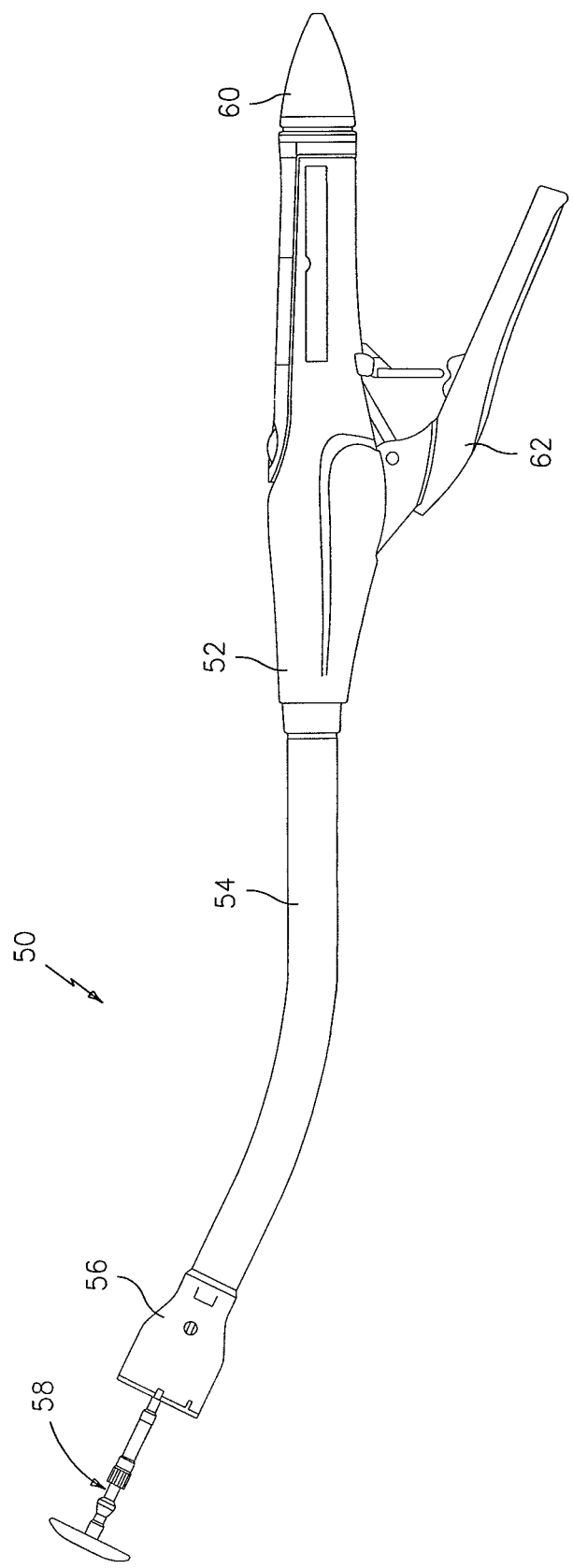
FIG. 2 is a side, elevational view of a conventional circular surgical stapling apparatus to be used in the sheath system in accordance with the embodiment of FIG. 1.

Also as seen in FIG. 1, and in particular in FIG. 2, a conventional surgical anastomosis apparatus is generally designated 50. Surgical anastomosis apparatus 50 includes a yoke 52, a pusher tube assembly 54 extending from yoke 52 to carry a staple assembly 56 at a distal end of pusher tube assembly 54, and an anvil assembly 58 at a distal end of apparatus 50. Apparatus 50 includes an actuating mechanism (not shown) extending proximally from anvil assembly 58 through pusher tube assembly 54 to a wing nut 60 at a proximal end of apparatus 50 for moving anvil assembly 58 against staple assembly 56. In addition, apparatus 50 includes at least one handle 62 configured and adapted to fire apparatus 50. A surgical apparatus similar to surgical anastomosis apparatus 50 disclosed herein is described in commonly assigned U.S. Pat. No. 5,392,979 to Green et al., the entire disclosure of which is hereby incorporated herein by reference. Although an anastomosis instrument is shown in FIG. 2, the sheath system may be used to introduce any surgical instrument.

Figure 3:
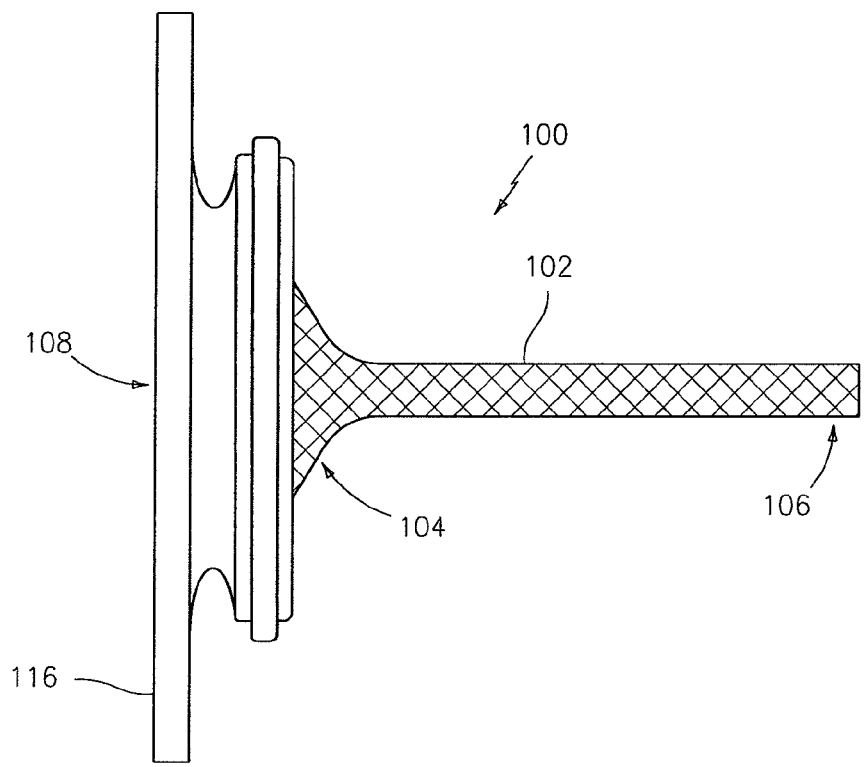
FIG. 3 is a side, elevational view of a radially expandable dilation assembly of the sheath system in accordance with the embodiment of FIGS. 1 and 2.
Figure 4:
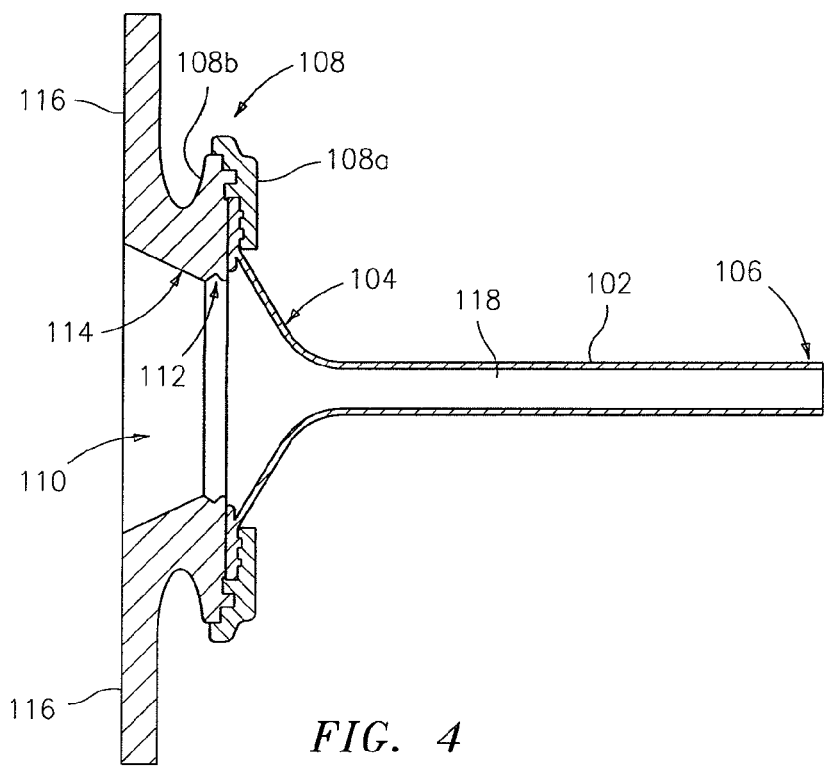
FIG. 4 is a cross-section side elevational view of the radially expandable dilation assembly, as taken along a longitudinal axis thereof, in accordance with the embodiment of FIGS. 1-3.

As seen in FIG. 1 and, in particular, in FIGS. 3 and 4, radially expandable dilation assembly 100 includes a tubular sheath 102 having a proximal end 104 and a distal end 106. Tubular sheath 102 defines a lumen 118 (see FIG. 4) therethrough. The proximal end 104 is tapered radially outward in the proximal direction and secured to a handle assembly 108, as best seen in FIGS. 3 and 4. An aperture 110 of handle assembly 108 (see FIG. 4) is preferably aligned with the expandable diameter of proximal end 104 of sheath 102. Aperture 110 preferably has a cross-sectional area which is larger than a cross-sectional area of lumen 118 while in a non-radially expanded condition. Aperture 110 has a first diameter and lumen 118 has a second diameter smaller than the first diameter.

Tubular sheath 102 may be made from any material which is capable of receiving the assembly of the dilator 30 and expansion assembly 400 to effect radial expansion of tubular sheath 102, as described in more detail hereinafter. Tubular sheath 102 may be as disclosed in certain embodiments of U.S. Pat. Nos. 5,431,676 and 5,183,464, the disclosures of which are hereby incorporated by reference herein. The tubular sheath is made from medical grade materials and may comprise an elastic membrane that expands in receiving expansion assembly 400. Preferably, tubular sheath 102 is made from an expandable tubular braid which is initially in an elongate, narrow-diameter configuration. The tubular braid may be open, but will often preferably be laminated or covered with a coating or layer of elastomeric or plastically deformable material, such as silicone, rubber, latex, polyurethane, polyethylene, C-flex (a silicone modified styrenic thermoplastic elastomer), or the like. The tubular braid is preferably formed as a mesh of individual filaments (e.g., composed of polyamide fiber such as Kevlar®, which is a trademark of E.I. DuPont De Nemours and Company and is commercially available from DuPont, stainless steel, or the like). The filaments are desirably inelastic so that radial expansion causes axial shortening of the tubular braid. Such axial shortening of the tubular braid, when tubular sheath 102 is penetrated into the surrounding body tissue, helps to anchor dilation assembly 100 in place within the patient's tissue and helps seal the exterior of dilation assembly 100 against the tissue. Such an anchored sheath with a gas-tight seal is a particular advantage in gastric and esophageal surgery, as well as other surgeries.

The tubular braid may be of conventional construction, including round filaments, flat or ribbon filaments, square filaments, or the like. Non-round filaments may advantageously reduce the axial force required to provide radial expansion. The filament width or diameter will typically be from about 0.002 inches to about 0.25 inches, and preferably between from about 0.005 inches to about 0.010 inches. Suitable braids may be obtained from a variety of commercial suppliers.

Dilation assembly 100 may optionally further include a sleeve (not shown) covering the braid of tubular sheath 102. The sleeve is preferably composed of a lubricous material, such as a thin-walled flexible plastic, such as polyethylene, tetraflourethylene, fluorinated ethylenepropylene, and the like. The sleeve surrounds tubular sheath 102 during initial insertion of dilation assembly 100 into the incision, but can be removed from tubular sheath 102 after dilation assembly 100 is in place in the incision. If desired, the sleeve is weakened along an axial line to facilitate splitting of the sleeve at some point during the procedure. For example, the sleeve may be split upon introduction of expansion assembly 400 into the dilation assembly.

As best seen in FIG. 4, handle assembly 108 of dilation assembly 100 preferably includes a distal handle member 108a and a proximal handle member 108b configured and adapted to be coupled to distal handle member 108a. The distal handle member 108a and proximal handle member 108b may be configured to snap together and/or may be glued together, or otherwise attached. Preferably, proximal end 104 of tubular sheath 102 is securely held between proximal and distal handle members 108a, 108b of handle assembly 108. Preferably, proximal handle member 108b of handle assembly 108 includes a thread 112 formed along an inner circumferential surface 114 thereof and a pair of laterally extending tabs 116.

Figure 5:
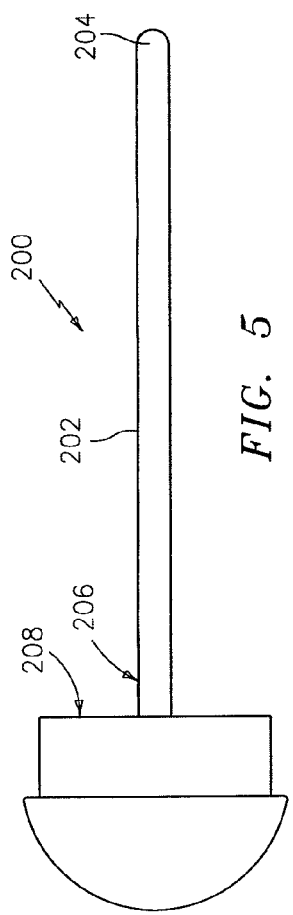
FIG. 5 is a side, elevational view of an introducer of the sheath system in accordance with the embodiment of FIGS. 1-4.

Referring now to FIGS. 1 and 5, introducer 200 includes a shaft 202 having a distal end 204 which is atraumatic and a proximal end 206 having a handle 208 mounted thereto. As seen in FIG. 5, atraumatic distal end 204 is shown as rounded (i.e., hemi-spherical), however, it is envisioned that distal end 204 of shaft 202 can be any atraumatic shape, including and not limited to, conical, pyramidal, blunt and the like. In further embodiments, introducer 200 has a penetrating or sharp distal end. Preferably, shaft 202 of introducer 200 has a cross-sectional area which is substantially equal to or less than the cross-sectional area of lumen 118 of tubular sheath 102. It is preferred that shaft 202 is solid. However, it is envisioned that shaft 202 can be hollow, or have one or more passages defined therein.

It is envisioned that handle 208 of introducer 200 is configured and dimensioned to be threadingly received within aperture 110 of handle assembly 108. Handle 208 may be provided with a thread (not shown) formed along an outer surface thereof. The thread of handle 208 engages thread 112 formed along circumferential surface 114 of handle assembly 108. In this manner, the relative position of introducer 200, with respect to dilation assembly 100 can be fixed. Introducer 200 may also be fixed using other means such as latches, bayonet-type fittings, etc., or may remain free to move with respect to dilation assembly 100.

Figure 6:
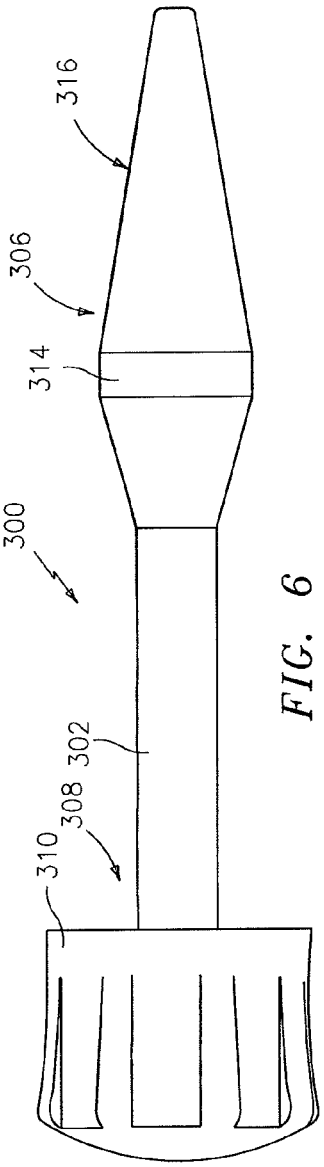
FIG. 6 is a side, elevational view of a dilator of the sheath system in accordance with the embodiment of FIGS. 1-5.
Figure 7:
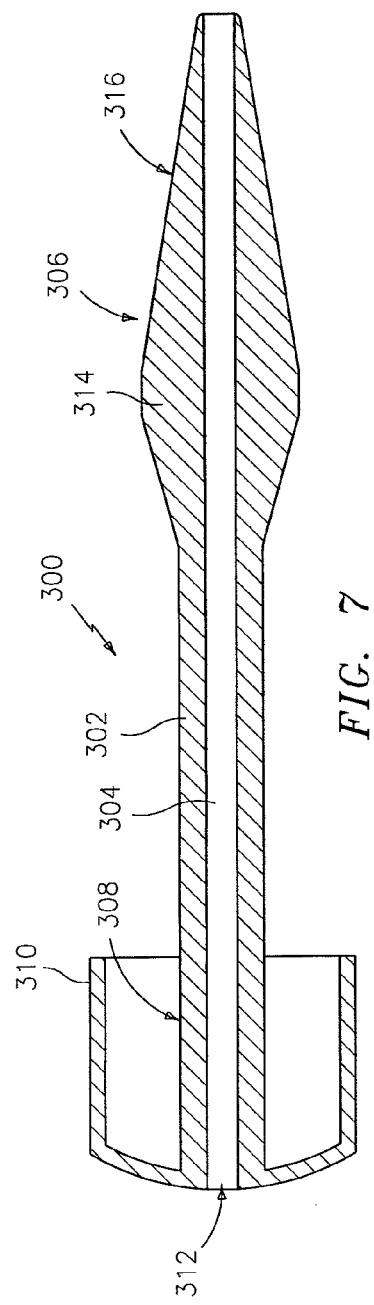
FIG. 7 is a cross-sectional view of the dilator of FIG. 6, taken along a longitudinal axis thereof, in accordance with the embodiment of FIGS. 1-6.

Referring now to FIGS. 1, 6 and 7, dilator 300 includes a rigid tubular member 302 defining a lumen 304 (see FIG. 7) therethrough. Dilator 300 has a distal end 306 and a proximal end 308 having a handle 310 integrally formed therewith. Handle 310 includes an aperture 312 formed therein which is aligned with lumen 304 of tubular member 302. Preferably, distal end 306 includes an annular region 314 having an enlarged diameter as compared to tubular member 302, and a distal tapered surface 316 which facilitates penetration/entry of dilator 300 into the patient's body. In particular, annular region 314 and distal tapered surface 316 act as a transition from the narrow diameter introducer 200 to the larger diameter expansion assembly 400.

Figure 8:
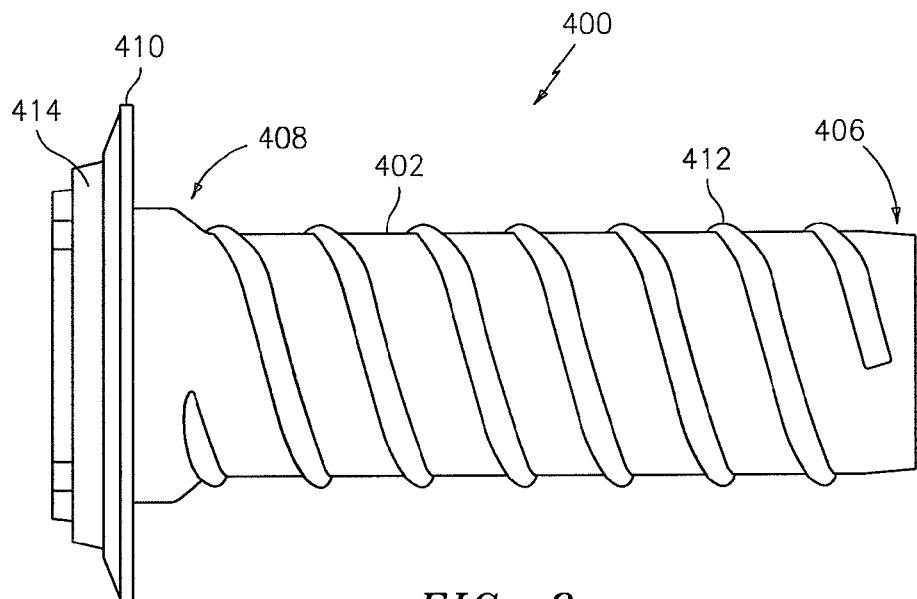
FIG. 8 is a side, elevational view of an expansion assembly of the sheath system in accordance with the embodiment of FIGS. 1-7.
Figure 9:
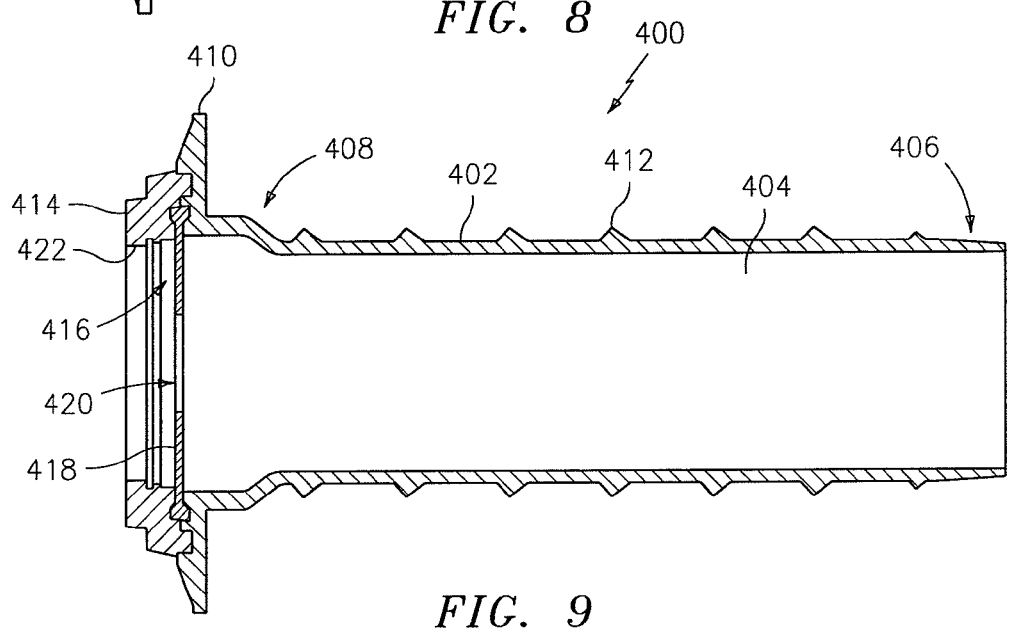
FIG. 9 is a cross-sectional view of the expansion assembly, taken along a longitudinal axis thereof, in accordance with the embodiment of FIGS. 1-8.

As seen in FIGS. 1, 8 and 9, expansion assembly 400 includes a rigid tubular member 402 defining a lumen 404 therethrough. Expansion assembly 400 has a distal end 406 and a proximal end 408. Tubular member 402 has an annular flange 410 integrally formed therewith, at proximal end 408. Preferably, tubular member 402 includes a helical thread 412 formed along an outer surface thereof. It is envisioned that tubular member 402 of expansion assembly 400 is configured and dimensioned to be threadingly received within aperture 110 of handle assembly 108. In particular, it is envisioned that helical thread 410 of tubular member 402 engages thread 112 formed on the inner surface 114 of handle assembly 108. As will be described in greater detail below, helical thread 410 and thread 112 create a mechanical advantage whereby rotation of expansion assembly 400 relative to dilation assembly 100 results in distal and/or proximal displacement of expansion assembly 400 axially through tubular sheath 102 of dilation assembly 100.

Preferably, tubular member 402 will have an overall cross-sectional area which is less than the cross-sectional area of aperture 110 of handle assembly 108 while lumen 404 of tubular member 402 will have a cross-sectional area which is greater than that of tubular sheath 102 of dilation assembly member 100 when in its non-radially expanded configuration. The diameter of tubular member 402 is less than first diameter of aperture 110 and greater than second diameter of lumen 118. Thus, as will be described in greater detail below, by introducing tubular member 402 of expansion assembly 400 through lumen 118 of tubular sheath 102 and causing tubular sheath 102 (e.g., the braid) to radially expand, an enlarged access channel is provided by lumen 404 of fixed-radius tubular member 402.

To facilitate introduction of expansion assembly 400 through lumen 118 of tubular sheath 102, dilator 300 is preferably inserted within and through lumen 404 of tubular member 402. Preferably, annular region 314 of dilator 300 has a diameter which is slightly smaller than the diameter of lumen 404 of tubular member 402 in order to permit passage of distal end 306 of dilator 300 through tubular member 402. Preferably, dilator 300 has a tapered surface 316 that extends distally from distal end 306 of dilator 300 and acts to gradually radially expand tubular sheath 102 as expansion assembly 400 is advanced therethrough. Dilator 300 can then be removed from expansion assembly 400 to leave lumen 404 of tubular member 402 unobstructed after expansion assembly 400 has been fully advanced through tubular sheath 102 of dilation assembly 100. The open lumen 404 provides access into the body.

Handle 310 of dilator 300 and proximal cap 414 desirably include inter-engaging threads, latches, or bayonet structures for attaching dilator 300 and expansion assembly 400.

Expansion assembly 400 includes a proximal end cap 414 in the form of a ring defining an aperture 416 therein. Aperture 416 of proximal end cap 414 is preferably aligned with lumen 404 of tubular member 402. Proximal end cap 414 is snap-fitted to, adhered to, or otherwise attached to flange 410 of tubular member 402. It is envisioned that expansion assembly 400 includes a seal 418 securely held between flange 410 and distal end cap 414. Preferably, seal 418 defines an aperture 420 which is aligned with lumen 404 of tubular member 402. Seal 418 may comprise a conventional septum seal of an elastomeric material.

Seal 418 is preferably capable of accommodating surgical instruments of varying diameters while providing a fluid-tight seal about the outer surface of the surgical instrument, regardless of the particular diameter of the surgical instrument. In this manner, when a surgical instrument is inserted into lumen 404 of tubular member 402, seal 418 reduces or eliminates the amount of insufflation gas escaping along the outer surface of the surgical instrument. For example, seal 418 is capable of creating a fluid-tight seal around pusher tube assembly 54 of surgical anastomosis apparatus 50.

Preferably, seal 418 is made from a resilient or elastomeric polymeric material, most preferably polyisoprene, or a combination of materials. It is contemplated that seal 418 may be provided with a layer of fabric disposed on either the proximal surface, the distal surface or on both the proximal and distal surfaces thereof. The fabric may be any suitable fabric, including spandex, lycra, nylon, or combinations thereof. It is further envisioned that seal 418 can include a fabric layer enveloped between upper and lower elastomeric layers. In further embodiments, proximal end cap 414 includes a further seal, for sealing lumen 404 in the absence of an instrument. For example, a duckbill or flapper valve may be used. Inflatable bladders, foam or coil valve arrangements may also be used, alone, or in combination with a further valve or valves.

It is envisioned that flange 410 extends radially outward from tubular member 402 thereby preventing expansion assembly 400 from fully entering dilation assembly 100. In other words, flange 410 acts like a stop which abuts against the surface of handle assembly 108 of dilation assembly 100 as tubular member 402 is distally advanced therethrough. In addition, flange 410 acts as a handle which the surgeon can grip in order to facilitate rotation of expansion assembly 400 relative to dilation assembly 100.

Figure 10:
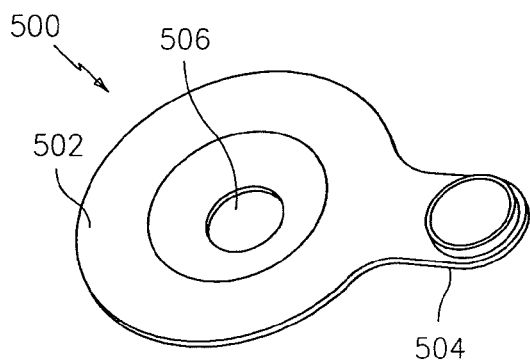
FIG. 10 is a perspective view of a detachable converter of the sheath system, in accordance with the embodiment of FIGS. 1-9.
Figure 11:
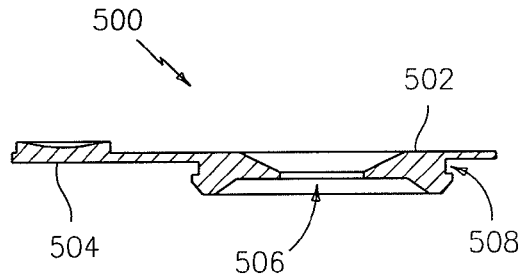
FIG. 11 is a cross-sectional view of the converter in accordance with the embodiment of FIGS. 1-10.

The sheath system desirably includes a converter for seal 418. Referring now to FIGS. 1, 10 and 11, converter 500 includes a substantially circular body portion 502 configured and dimensioned to cover aperture 416 of distal end cap 414, a finger tab 504 extending radially outward from body portion 502 to facilitate attachment of converter 500 to and removal of converter 500 from distal end cap 414 of expansion assembly 400, and an aperture 506 formed in body portion 502 which is substantially aligned with lumen 404 of tubular member 402 when converter 500 is attached to distal end cap 414. Preferably, aperture 506 of converter 500 has a cross-sectional area which is less than a cross-sectional area of aperture 420 of seal 418 so that expansion assembly 400 sealingly receives instruments smaller than seal 418. Body portion 502 of converter 500 includes an annular recess 508 formed therein. In use, annular recess 508 of converter 500 is configured and dimensioned to engage an annular rim 422 formed along an inner periphery of distal end cap 414 (see FIG. 9). It is contemplated that converter 500 is made from polymeric material, preferably a thermoplastic elastomer, such as, for example, a thermoplastic rubber.

Figure 12:
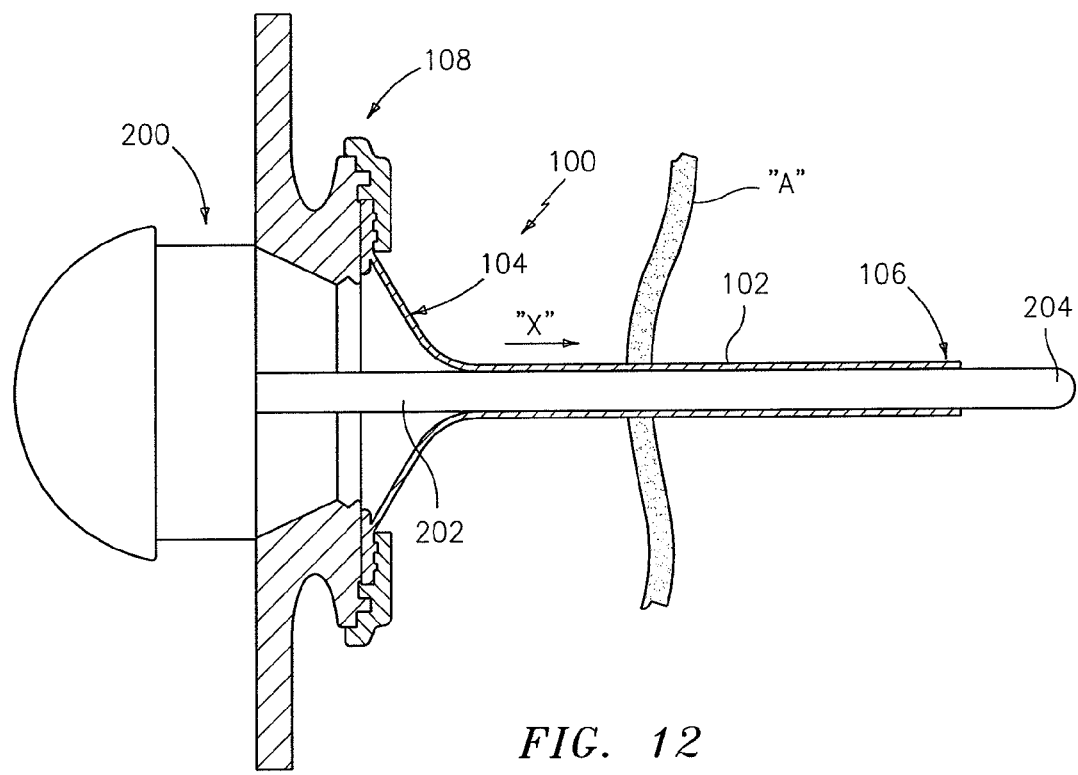
FIGS. 12-18 illustrate use of the sheath system in accordance with the embodiment of FIGS. 1 and 3-11 in providing access to a body cavity of a patient.

Referring now to FIGS. 12-18, use of the sheath system of the present disclosure in laparoscopic surgery will be described in detail. Initially, as seen in FIG. 12, use of sheath system 200 includes assembling introducer 200 and dilation assembly 100, and introducing the combination of radially expandable dilation assembly 100 and introducer 200 into and though an opening formed in an abdominal wall "A" of a patient (or other body location) by inserting distal end 204 of introducer 200 and distal end 106 of dilation assembly 100 through abdominal wall "A" into the abdomen and advancing introducer 200 and dilation assembly 100, in direction "X", until tubular sheath 102 extends across the abdominal wall "A". Introducer 200 can include a blunt or flattened tip and, after an incision is made in the skin, the blunt tip of introducer 200 can be utilized to deflect fascia and muscle of the abdominal wall. The tip may be rounded, as shown in FIGS. 1 and 3-18, for example, conical or any other shape suitable for tissue deflecting tissue.

Figure 13:
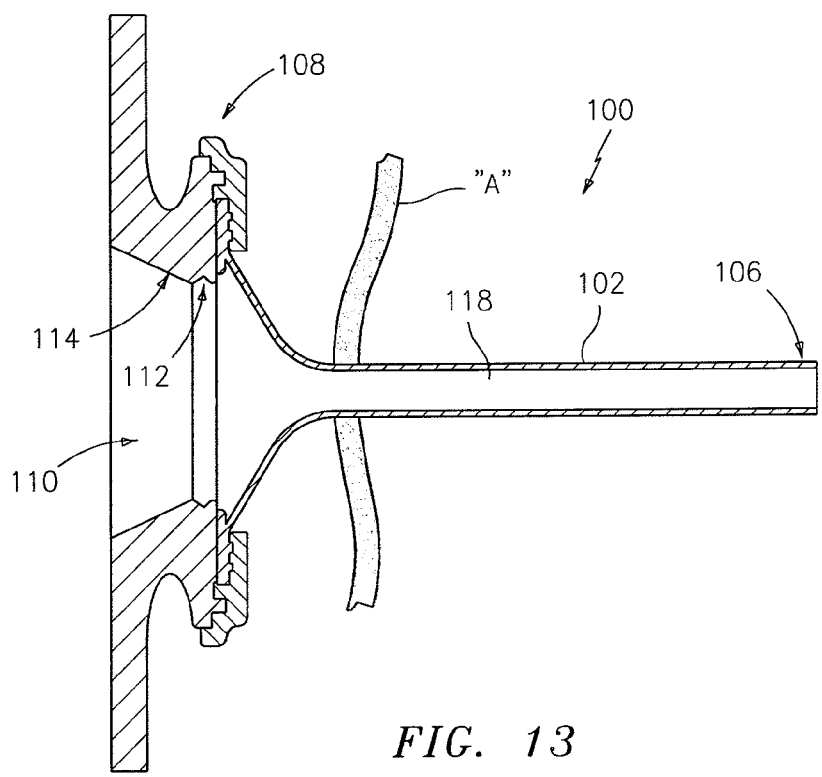
Figure 14:
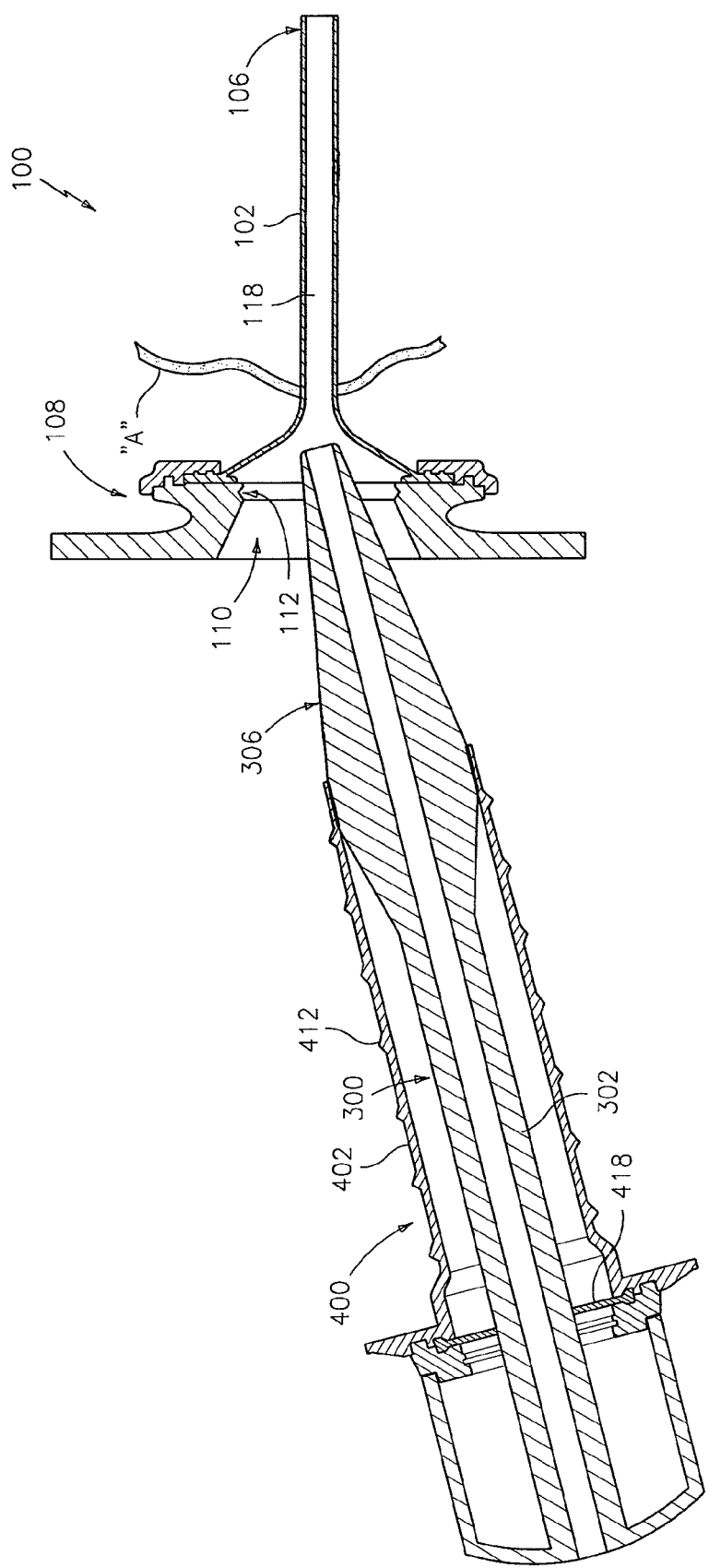
Figure 15:
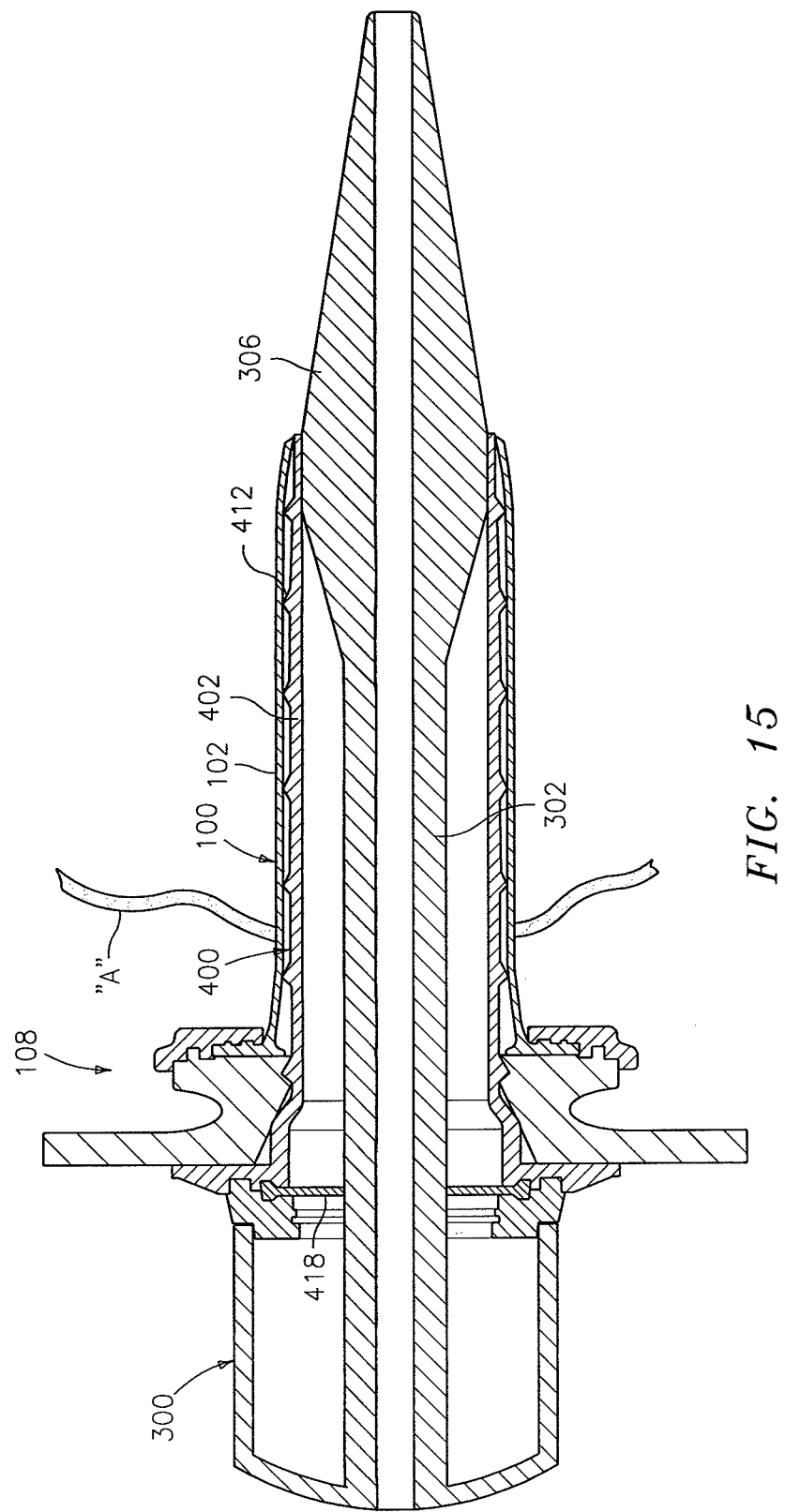

Turning now to FIG. 13, introducer 200 is withdrawn from dilation assembly 100 thus leaving lumen 118 of dilation assembly 100 extending across abdominal wall "A". As seen in FIG. 14, an expansion assembly 400, having a dilator 300 inserted through tubular member 402 of expansion assembly 400, is introduced into aperture 110 of handle assembly 108 of dilation assembly 100. In particular, distal end 306 of dilator 300 and distal end 406 of expansion assembly 400 are inserted into aperture 110 of handle assembly 108 of dilation assembly 100 until the distal end of helical thread 412 engages thread 112 formed along circumferential surface 114 of handle assembly 108. By holding handle assembly 108 of dilation assembly 100 and rotating at least expansion assembly 400 about a longitudinal axis thereof, dilator 300 and expansion assembly 400 are distally drawn/advanced through tubular sheath 102 of dilation assembly 100, resulting in radial expansion of tubular sheath 102 along the length thereof (see FIG. 15) as well as the radial expansion of the opening formed in abdominal wall "A". As expansion assembly 400 is rotated, the operator holds dilation assembly 100 in place.

Figure 16:
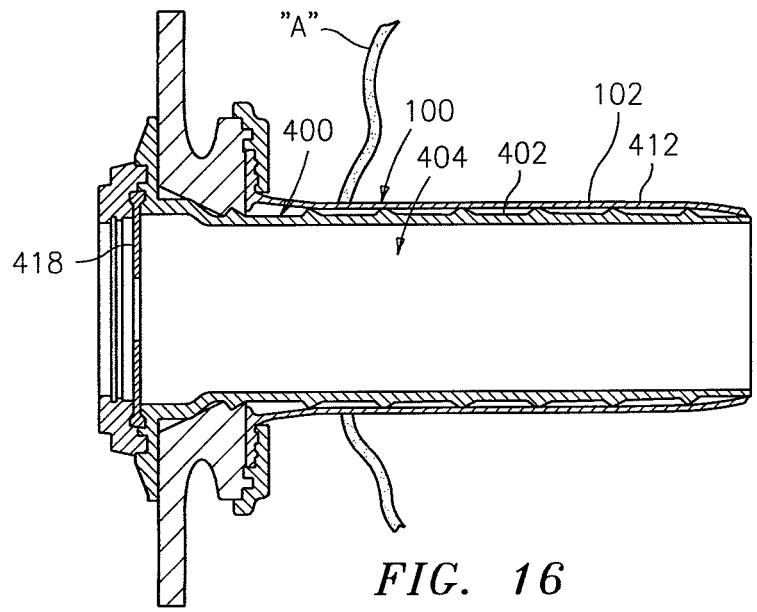
Figure 17:
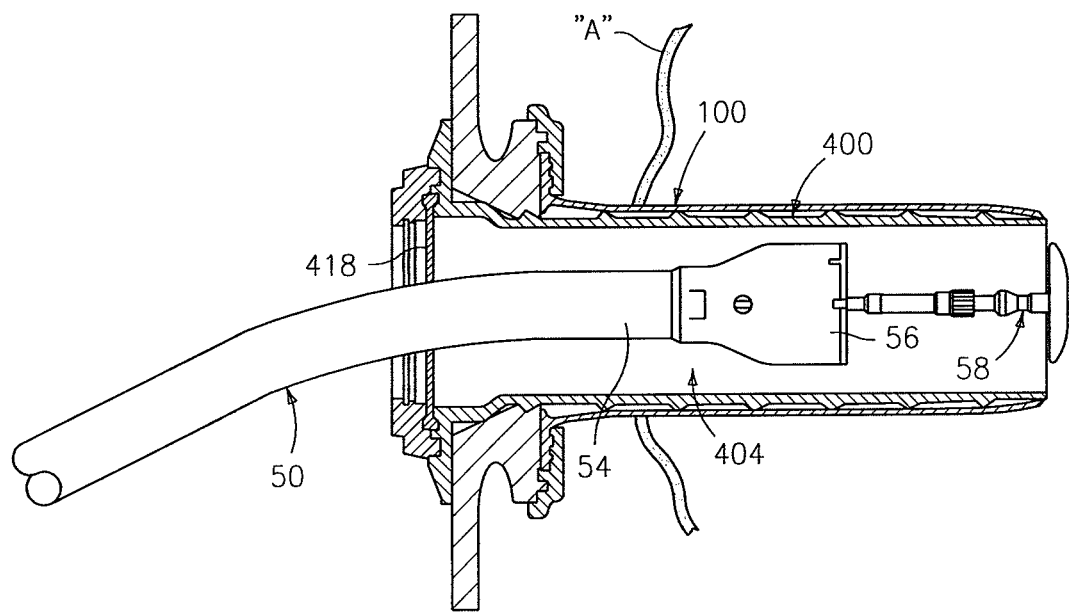

As seen in FIG. 16, dilator 300 is then withdrawn from expansion assembly 400 leaving an access channel across abdominal wall "A", as defined by lumen 404 of expansion assembly 400, from the outside of the patient's body to the desired internal location. Accordingly, by way of example only, with dilation assembly 100 and expansion assembly 400 in place in abdominal wall "A", a surgical instrument, such as, for example, surgical anastomosis apparatus 50 can be inserted therethrough to access the target surgical site (FIG. 17). Preferably, as described above, seal 418 creates a substantially fluid-tight seal around pusher tube assembly 54 of surgical anastomosis apparatus 50 thereby effectively reducing the escape of insufflation gases along the exterior surface of pusher tube assembly 54.

Figure 18:
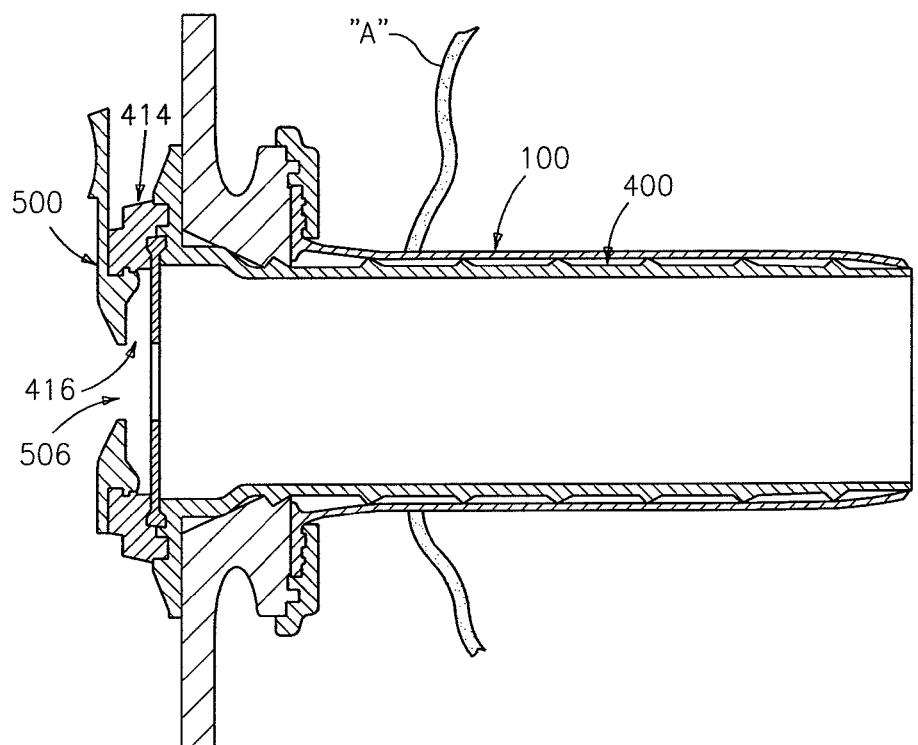

Turning now to FIG. 18, in the event that a surgical instrument, having a diameter which is smaller than the size of aperture 400 of seal 418, is desired to be used, converter 500 is attached to distal end cap 414. As such, the size of aperture 416 of expansion assembly 400 is reduced in order to accommodate the smaller diameter surgical instruments.

In a further embodiment of the disclosure, the sheath system is inserted in a naturally occurring orifice in the body and used to guide insertion into the body. The steps in a method of doing so are as discussed above in connection with FIGS. 12-17.

Figure 19:
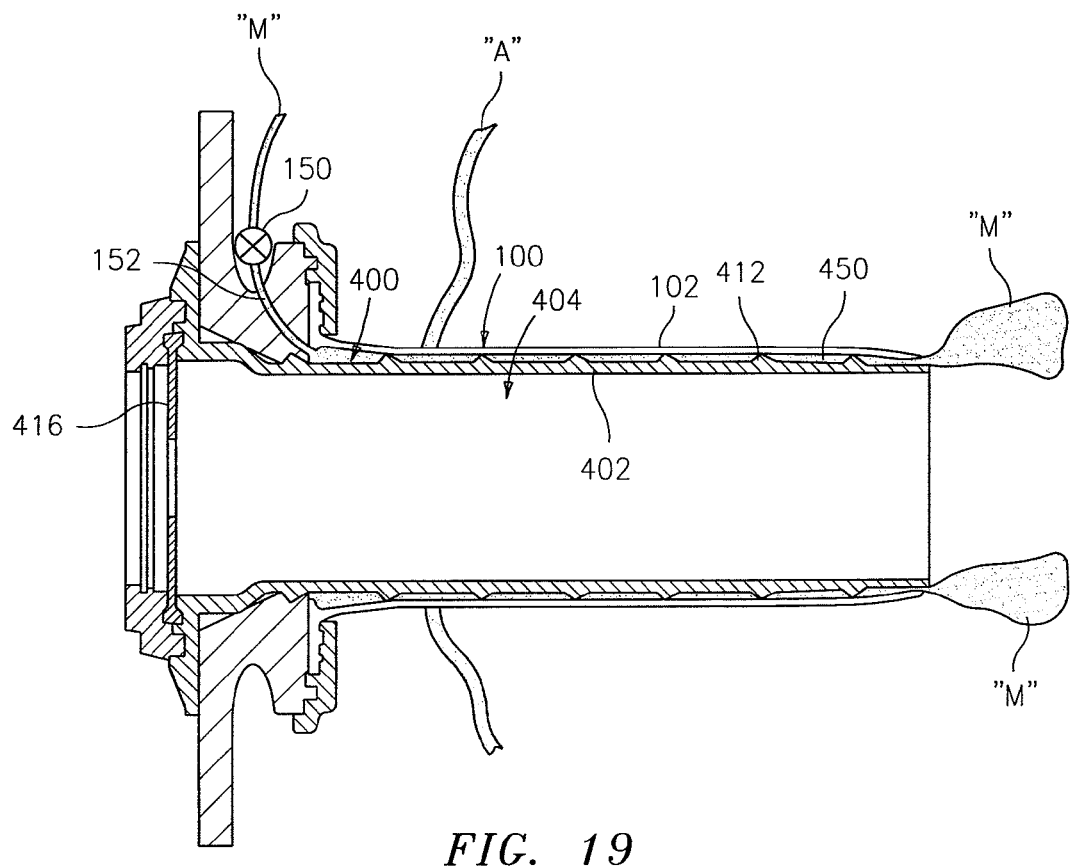
FIG. 19 is a cross-sectional view of a further embodiment of a sheath system, illustrating a method of use thereof.

In accordance with a further embodiment of the present disclosure, and as seen in FIG. 19, it is envisioned that handle assembly 108 of expansion assembly 100 is provided with a valve stem 150 operatively coupled thereto. Valve stem 150 includes a lumen 152 extending therethrough and opening into aperture 110, preferably, at a location distal of thread 112. Accordingly, during use, if desired, a surgeon can inject a medicament "M" into aperture 110 of expansion assembly 100, via lumen 152. As seen in FIG. 19, since helical thread 412 of dilation assembly 400 causes tubular braid 102 of expansion assembly 100 to tent up and define a helical passageway 450 extending distally through lumen 118 of threaded braid 102, medicament "M" is forced distally therethough as a result of the injection pressure of the medicament. Medicament "M" will travel distally through passageway 450 until it exits from distal end 106 of tubular braid 102. Other medicament delivery arrangements are shown and described in commonly assigned International Application Serial No. PCT/US02/24308, filed Jul. 31, 2002, entitled "Apparatus and Method for Providing Percutaneous Access and Medicament to a Target Surgical Site", the entire contents of which are incorporated herein by reference.

Sheath system 10 effectively radially enlarges openings formed through the patient's skin (e.g., the abdominal wall), or a naturally occurring orifice in the body, in order to accommodate larger surgical instruments, such as, for example, circular stapling instruments, endoscopic stapling instruments, surgical retractors and the like.

While the sheath system according to the present disclosure obtains its mechanical advantage from a pair of cooperating threads, one formed on each of expansion assembly 100 and dilation assembly 400, it is envisioned that other modes of creating a mechanical advantage, to facilitate the distal advancement of dilation assembly 400 through expansion assembly 100, are possible. For example, the sheath system disclosed herein can obtain a mechanical advantage by providing tubular member 402 of dilation assembly 400 with a plurality of radially disposed longitudinal ribs, a plurality of nubs and/or a plurality of thread-like ribs formed thereon which effectively reduce the amount of surface in contact with one another and thus the insertion force required.

Figure 20:
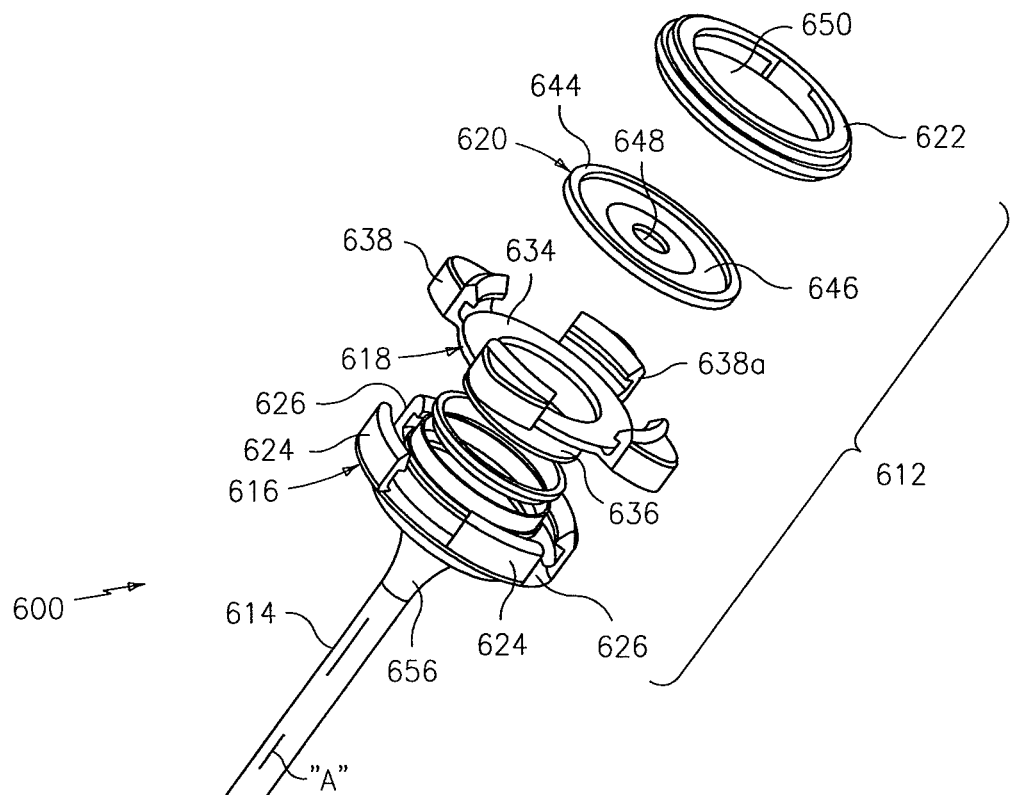
FIG. 20 is an exploded perspective view of a radially expandable dilation assembly in accordance with a further embodiment of the present disclosure.
Figure 21:
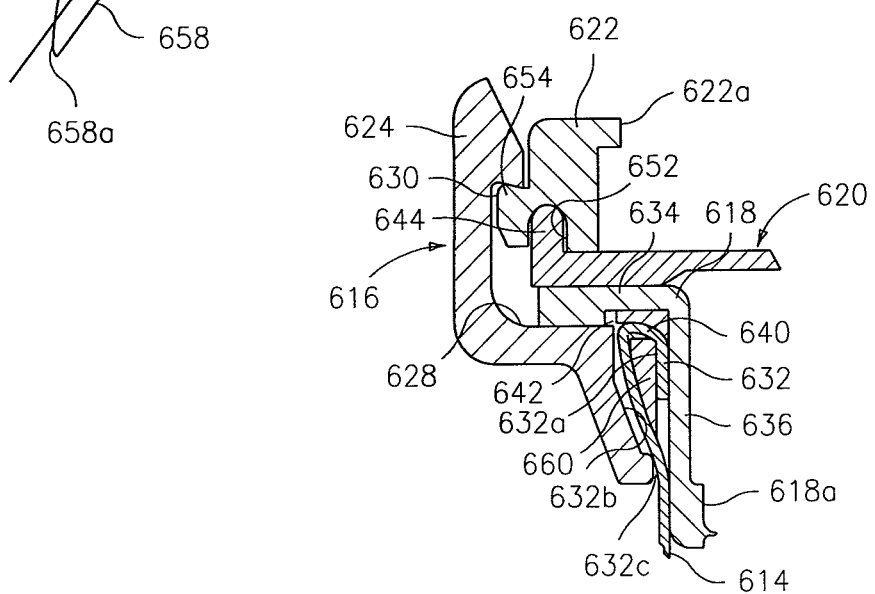
FIG. 21 is an enlarged cross-sectional view of the proximal end of the radially expandable dilation assembly of FIG. 21.

In a further embodiment of the sheath assembly, as seen in FIGS. 20 and 21, dilation assembly 600 generally includes a housing 612 and an elongate member 614 extending from housing 612. Housing 612 and elongate member 614 define a longitudinal axis "A" which extends through and along the length of dilation assembly 600.

With continued reference to FIGS. 20 and 21, housing 612 includes several components, which, when assembled, define a structure advantageously dimensioned to be held by the surgeon. These components include a base 616, a hub 618, a seal 620 and a cover 622. Base 616 defines an outer wall 624 having a plurality of spaced recesses 626 therein. Recesses 626 are generally rectangular in configuration as shown. The interior of base 616 has a transverse ledge 628 upon which hub 618 rests and a locking shelf 630 adjacent the proximal end of base 616. Base 616 defines a distal tapered portion 632 which tapers inwardly relative to the longitudinal axis "X". In a preferred embodiment, tapered portion 632 incorporates a pair of intersecting surfaces 632a, 632b and a transverse shelf 632c. Tapered portion 632 functions in securing elongate member 614 to base 616 as will be discussed.

Hub 618 of housing 612 includes a disc-shaped portion 634 and an annular wall 636 extending distally from disc-shaped portion 634. Disc-shaped portion 634 has a plurality of vertical locks 638 extending upwardly from disc-shaped portion 634. Vertical locks 638 are received within correspondingly positioned and dimensioned recesses 626 of base 616 in the assembled condition of housing 612. Vertical locks 638 each have an internal locking shelf 638a, which align with shelves 630 of base 616. Annular wall 636 of hub 618 is generally continuous and defines a diameter which is less than the effective internal diameter of base 616, and/or the effective diameter of the proximal end of elongate member 614. Annular wall 636 is received within base 616 and elongate member 614 upon assembly of device 600. Hub 618 further includes a resilient seal or O-ring 640 which is accommodated within groove 642 disposed on the underside of hub 618. O-ring 640 is adapted to form a gas-tight seal between hub 618 and base 616.

With continued reference to FIGS. 20 and 21, seal 620 includes an outer circumferential wall 644 and an inner seal portion 646 extending radially inwardly relative to longitudinal axis "A". Inner seal portion 646 defines a central aperture 648 which is dimensioned for passage of an object, e.g., a surgical instrument, guide wire, catheter or the hand of a surgeon. Seal 620 may be fabricated from any elastomeric material suitable for its intended purpose. A friction reducing coating may be applied to seal 620. Other valve types are also contemplated including zero-closure valves, slit valves, septum valves, double-slit valves, inflatable bladders, foam or gel valve arrangements, etc.

Cover 622 has a generally annular shape as shown defining a central opening 650 for permitting passage of the object therethrough. Cover 622 includes a circumferential recess 652 on its underside or distal end face which accommodates outer circumferential wall 644 on seal 620. The peripheral area of cover 622 defines a ledge or shelf 654 which, in the assembled condition, engages locking shelf 630 of base 616 and/or locking shelf 638a of vertical locks 638 of hub 618 in snap relation therewith to thereby secure the remaining components of housing 612 within base 616. Other mechanical arrangements for securing cover 622 to base 616 are also envisioned including, e.g., a screw thread arrangement, bayonet-type coupling, etc.

The components of housing 612 may be fabricated from any suitable generally rigid material (notwithstanding the seal) including stainless steel, titanium or a rigid polymeric material. The components of housing 612 may be fabricated from any suitable medical grade material.

Referring still to FIGS. 20 and 21, elongate member 614 will be discussed. Elongate member 614 defines a general tubular shape having a proximal end 656 and a distal end 658. Proximal end 656 is flared radially outward in a proximal direction and secured to housing 612. Distal end 658 includes an inclined surface 658a obliquely arranged relative to longitudinal axis "X". Inclined surface 658a facilitates passage of elongate member 614 through the tissue. Tubular elongate member 614 may be fabricated from any material which is capable of radial expansion of elongate member 614. The materials include the materials disclosed above with respect to tubular sheath 102. It is also envisioned that a polyethylene sheath may be assembled over elongate member 614. Elongate member 614 may comprise an elastomeric member or members without the braided material. Embodiments may include a material incorporating filaments, where the filaments may be elastic, in elastic, monofilaments, multifilaments, braided, woven, knitted or non-woven material with or without an elastomeric membrane.

Desirably, elongate member 614 comprises an expandable braid that is laminated or covered with a coating or layer of elastomeric or plastically deformable material, as discussed above in connection with tubular sheath 102. Desirably, the elastomeric or plastically deformable material is formed with an enlarged proximal end, which facilitates moving elongate member 614 to housing 612, as disclosed in U.S. Provisional Application 60/512,548 entitled "Surgical Access Device and Manufacture Thereof", filed Oct. 17, 2003 by Miguel A. Moreno, Richard D. Gresham, and Thomas Wenchell, the entire disclosure of which is hereby incorporated by reference herein.

With particular reverence to FIG. 4, elongate member 614 has a mounting element or ring 660 which is anchored within elongate member 614 adjacent proximal end 656. Mounting ring 660 is respectively retained within proximal end 656 of elongate member 614 through a frictional arrangement or relationship created between proximal end 56 of elongate member 14 and the mounting ring 660. Mounting ring 660 assists in securing elongate member 614 to housing 612 by being captured between base 616 and hub 618.

Dilation assembly 600 is used in the sheath system 10 of FIGS. 1 and 3-11 and used in a manner similar to the method shown in FIGS. 12-18.

Figure 23:
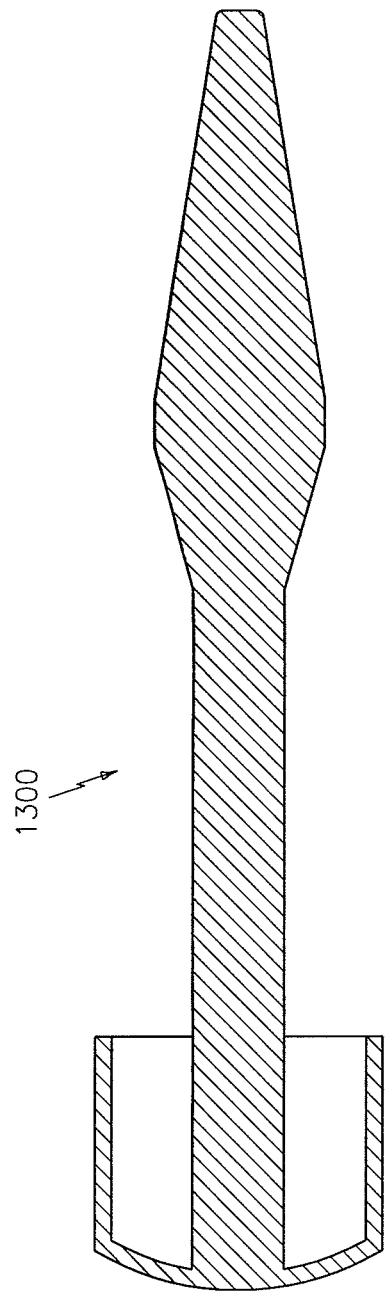
FIG. 23 is a cross-sectional view of the dilator, in accordance with another embodiment of the present disclosure, taken along a longitudinal axis thereof.
Figure 24:
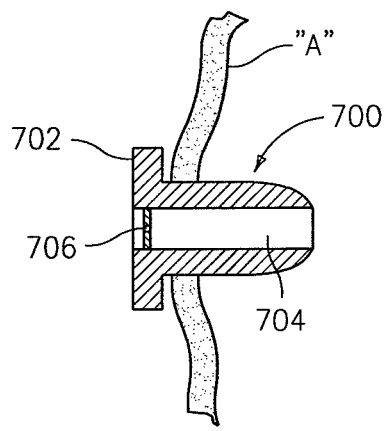
FIGS. 24-29 illustrate an alternate method of use of the sheath system of FIGS. 1 and 3-11 in providing access to a body cavity of a patient.
Figure 25:
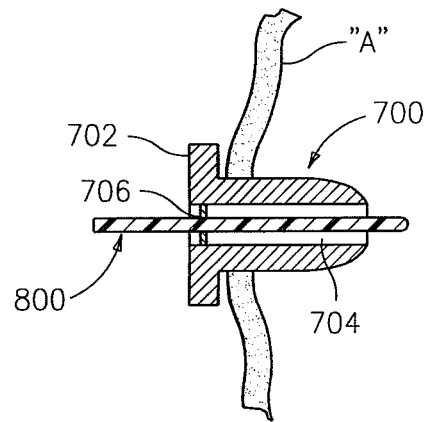
Figure 26:
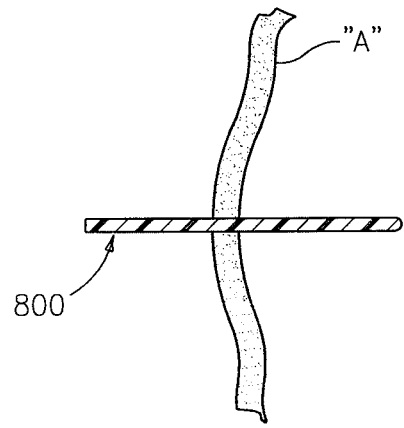
Figure 27:
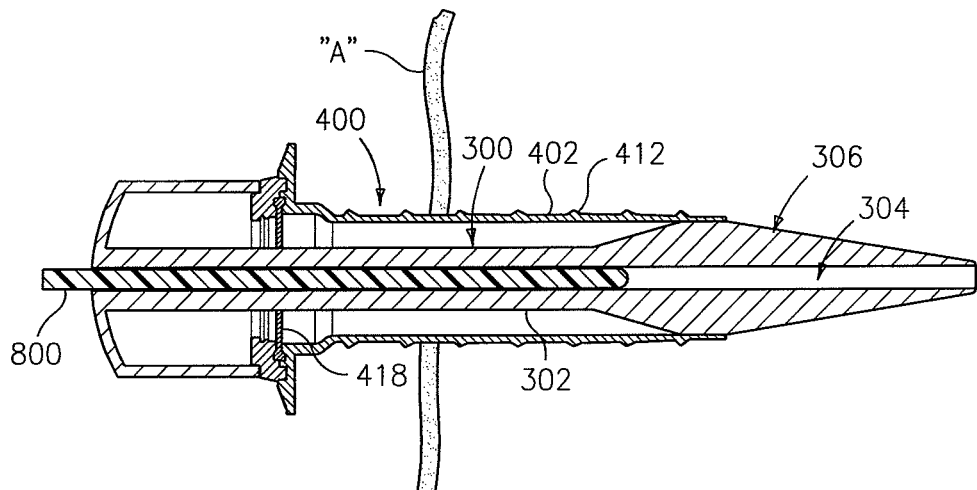
Figure 28:
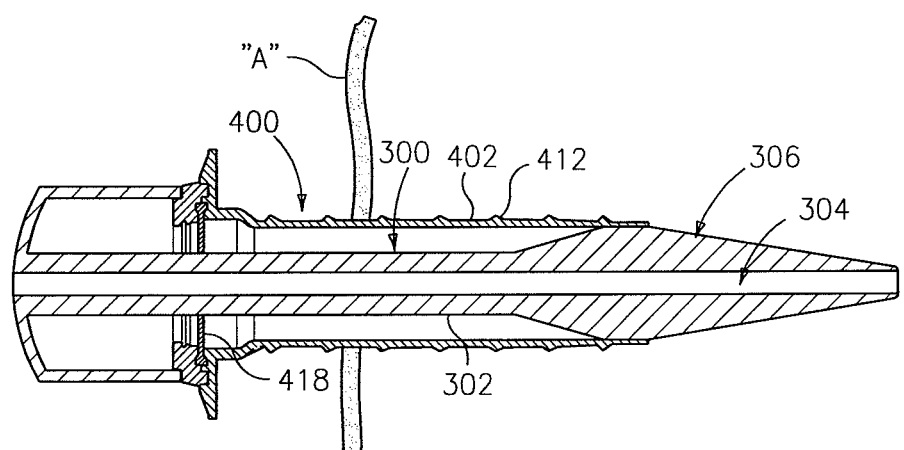
Figure 29:
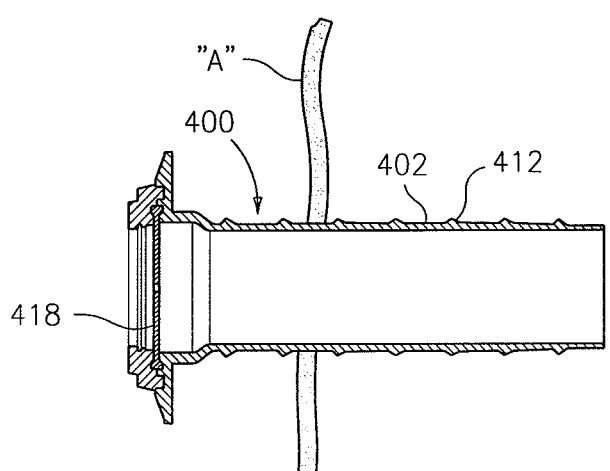

In a further embodiment of the present disclosure, it is envisioned that dilator 1300 can be a solid shaft, e.g., does not include lumen 304 extending therethrough (FIG. 23). Alternatively, the shaft of dilator 300 can be hollow and not be provided with any distal and/or proximal openings.

Figure 22:
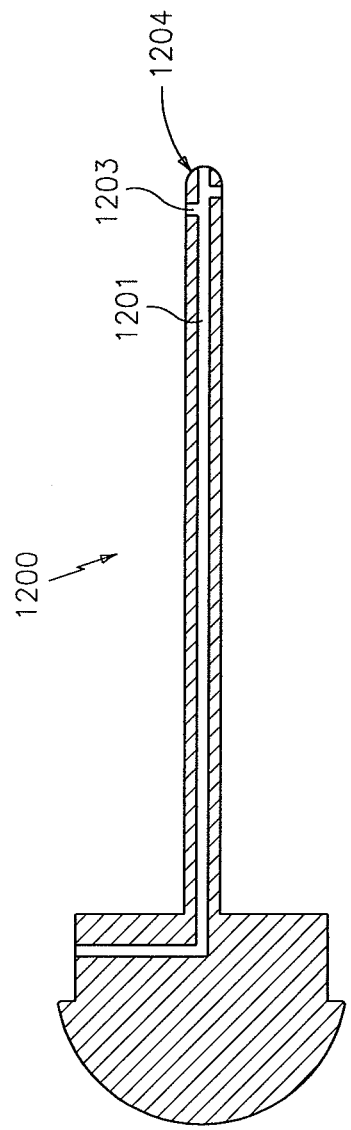
FIG. 22 is a longitudinal cross-sectional view of an introducer in accordance with another embodiment of the present disclosure.

In a further embodiment of the present disclosure, as seen in FIG. 22, introducer 1200 can include a passage 1201 extending at least substantially down its length and terminating in one or more openings 1203 adjacent distal end 1204. For example, introducer 1200 may have an opening at the distal-most part of distal end 1204, or on a side surface adjacent distal end 1204 or both. Introducer 1200 can be utilized to insufflate the body cavity, e.g., the abdominal cavity. In use, expansion assembly 400, having dilator 300 assembled therewith, is advanced into the lumen 118 of the radially expandable dilation assembly 100, as discussed above in connection with FIGS. 12-18. Preferably, in this embodiment, dilator 300 is a solid shaft dilator 1300, i.e., not having a lumen extending therethrough (see FIG. 23). Thread 412 of tubular member 402 and thread 112 of handle assembly 108 may be omitted in this embodiment, or may be included to provide the mechanical advantage discussed above. In this embodiment, after an incision is made in the skin of the patient, introducer 1200 is utilized to deflect fascia and muscle of the abdominal wall and optionally to insufflate the body cavity. In further embodiments, introducer 1200 comprises a blunt rod.

In another embodiment of the present disclosure, as seen in FIGS. 24-29, an alternative surgical procedure, utilizing a small port 700, is shown and described. Port 700 is a conventional trocar port, having a proximal seal housing 702 defining a lumen 704 and including one or more seals 706 operatively associated therewith to enable the use of instruments in an insufflated body cavity, without significant loss of insufflation gas. Port 700 generally has a smaller size in cross-section, as compared to the range of sizes of such ports typically used, such as a 5 mm port. With port 700 extending across abdominal wall "A" (see FIG. 24), a rod 800 is inserted into lumen 704 of port 700 (see FIG. 25) and port 700 is then removed over rod 800 (see FIG. 26). Rod 800 maintains the incision formed in abdominal wall "A" in an open condition until expansion assembly 400 and dilator 300 are inserted into the incision, over rod 800 (see FIG. 27). The expansion assembly and dilator are as discussed above in connection with FIGS. 1 and 3-11. Lumen 304 of dilator 300 receives rod 800 as expansion assembly 400 and dilator 300 are inserted. Then, rod 800 is removed (see FIG. 28). Dilator 300 is then removed from the expansion assembly 400 (see FIG. 29). Desirably, lumen 304 of dilator 300 is approximately the same size as rod 800 and the taper of dilator 300 expands the incision formed in abdominal wall "A" to the size of the larger diameter of tubular member 402.

While the above description of the use of sheath system 10 relates primarily to the expansion of an opening (e.g. percutaneous opening) formed in the abdominal wall, it is envisioned and within the scope of the present disclosure to include use of sheath system 10 in connection with corporal orifices (e.g., the anus, the vagina and the like).

While the above is a complete description of the preferred embodiments of the disclosure, various alternatives, modifications and equivalents may be used. Therefore, the above description should not be taken as a limitation to the scope of the disclosure which is defined by the appended claims.

What is claimed is:

1. A sheath system for enabling access through an opening in the body of a patient, the sheath system comprising:
   a dilation assembly having a radially expandable tubular sheath defining a lumen having a first cross-sectional area when in a non-expanded condition, and a handle assembly operatively coupled to a proximal end of the tubular sheath;
   a fluid delivery system supported on the dilation assembly, the fluid delivery system defining a fluid passage extending through the handle assembly of the dilation assembly, wherein an inlet of the fluid passage is located on an outer surface of the handle assembly and an outlet of the fluid passage opens into the lumen of the dilation assembly; and
   an expansion assembly including a tubular member defining a lumen having a second cross-sectional area which is larger than the first cross-sectional area of the tubular sheath of the dilation assembly, the tubular member having an outer surface defining a first thread formed along substantially an entire length of the tubular member from a location at least in close proximity to a distal end of the tubular member to a location in close proximity to a proximal end of the tubular member, wherein the first thread of the tubular member of the expansion assembly tents the radially expandable tubular sheath of the dilation assembly radially away from the tubular member to thereby define a helical passageway therearound for communicating a fluid from outside a target surgical site to the target surgical site.

2. The sheath system according to claim 1, wherein the handle assembly defines an aperture formed therein, and a second thread defined on a wall of the handle assembly that defines the aperture thereof; and wherein the first thread is arranged for engaging the second thread to axially advance the tubular member along the entire length thereof through the tubular sheath.

3. The sheath system according to claim 1, wherein the fluid delivery systems includes a valve stem fluidly connected to the inlet of the fluid passage.

4. The sheath system according to claim 1, further comprising a source of a fluid medicament connected to the inlet of the fluid passage of the fluid delivery system.

5. The sheath system according to claim 1, further comprising an introducer sized for receipt in the lumen of the radially expandable sheath, when the radially expandable sheath is in the non-expanded condition.

6. The sheath system according to claim 1, wherein the tubular sheath of the dilation assembly comprises a mesh of individual filaments.

7. The sheath system according to claim 6, wherein the filaments are inelastic so that radial expansion of the tubular sheath causes axial shortening of the tubular sheath.

8. The sheath system according to claim 6, wherein the tubular sheath comprises a tubular braid of individual filaments.

9. The sheath system according to claim 1, further comprising a seal at the proximal end of the expansion assembly.

10. The sheath system according to claim 9, wherein the seal is made from at least one of an elastomeric polymeric material and polyisoprene.

11. The sheath system according to claim 1, further comprising a dilator configured and dimensioned to be removably received within the lumen of the tubular member of the expansion assembly.

12. The sheath system according to claim 11, wherein a distal end of the dilator is tapered and defines threads.

13. The sheath system according to claim 12, wherein the dilator has a length such that when the dilator is received within the lumen of the tubular member, the tapered distal end thereof extends beyond a distal end of the tubular member.

14. The sheath system according to claim 1, further including an introducer having a shaft, wherein the shaft of the introducer has a length such that when the introducer is received within the lumen of the tubular sheath, a distal end thereof extends beyond a distal end of the tubular sheath.

15. The sheath system according to claim 9, further comprising a converter configured and dimensioned to be removably attached to a proximal end of the expansion assembly, the converter including an aperture formed therein, the aperture of the converter having a cross-sectional area less than a cross-sectional area of the opening formed in the seal of the expansion assembly.

16. A method of using a sheath system to enable access through an opening in the body of a patient, comprising:
   providing a dilation assembly including a housing defining an aperture and a first thread in the aperture, and a radially expandable sheath extending from the housing and defining a lumen that is aligned with the aperture of the housing, the radially expandable sheath having a first cross-sectional dimension;
   inserting the radially expandable sheath of the dilation assembly into the opening in the body of the patient;
   providing an expansion assembly including a substantially rigid tubular member with an outer surface defining a second thread formed along substantially an entire length of the tubular member from a location at least in close proximity to a distal end of the tubular member to a location in close proximity to a proximal end of the tubular member;
   introducing the expansion assembly into the lumen of the radially expandable sheath of the dilation assembly to radially expand the lumen of the radially expandable sheath of the dilation assembly and the opening in the body of the patient, the introduction including engaging the first thread with the second thread to axially advance the tubular member along the entire length thereof through the tubular sheath, wherein the second thread of the tubular member of the expansion assembly tents the radially expandable sheath of the dilation assembly radially away from the tubular member to thereby define a helical passageway therearound for communicating a fluid from outside the body of the patient to a location inside the body of the patient; and injecting a fluid into a proximal end of the helical passageway that is disposed outside of the body of the patient to communicate the fluid to the location inside the body of the patient via the helical passageway.

17. The method according to claim 16, further comprising inserting an introducer into the dilation assembly prior to the step of inserting the dilation assembly.

18. The method according to claim 16, further comprising inserting a dilator into the expansion assembly prior to the step of introducing the expansion assembly.

19. The method according to claim 16, wherein the lumen of the dilation assembly has a first cross-sectional area and the lumen of the expansion assembly has a second cross-sectional area which is larger that the first cross-sectional area of the lumen of the dilation assembly.

20. The method according to claim 19, wherein the sheath is made from a mesh of individual filaments.

21. The method according to claim 20, wherein radial expansion of the tubular sheath causes axial shortening of the sheath.

22. The method according to claim 16, wherein introducing the expansion assembly includes distal advancement of the tubular member of the expansion assembly through the sheath of the dilation assembly, resulting in radial expansion of the sheath.

23. The method according to claim 16, wherein engaging the first thread with the second thread includes rotation of the tubular member with respect to the dilation assembly.

24. The method according to claim 16, wherein the expansion assembly includes a seal disposed across the lumen of the tubular member, the seal including an opening formed therein, and the method further includes introducing an instrument into the tubular member through the opening of the seal.

25. The method according to claim 24, further comprising the step of removably attaching a converter to a proximal end of the tubular member, wherein an opening formed in the converter has a cross-sectional area which is less than the cross-sectional area of the opening formed within the seal.

* * * * *